US008329716B2

(12) United States Patent
Schirok et al.

(10) Patent No.: US 8,329,716 B2
(45) Date of Patent: *Dec. 11, 2012

(54) HETARYLOXY-SUBSTITUTED PHENYLAMINO PYRIMIDINES AS RHO KINASE INHIBITORS

(75) Inventors: Hartmut Schirok, Wuppertal (DE); Martin Radtke, Erkrath (DE); Joachim Mittendorf, Wupptertal (DE); Raimund Kast, Wuppertal (DE); Johannes-Peter Stasch, Solingen (DE); Mark Jean Gnoth, Mettmann (DE); Klaus Münter, Wülfrath (DE); Dieter Lang, Velbert (DE); Santiago Figueroa Perez, Leverkusen (DE); Michael Thutewohl, Buchs (CH); Samir Bennabi, Caluire et Cuire (FR); Heimo Ehmke, Hamburg (DE)

(73) Assignee: Bayer Intellectual Property GmbH, Monheim (DE)

( * ) Notice: Subject to any disclaimer, the term of this patent is extended or adjusted under 35 U.S.C. 154(b) by 842 days.

This patent is subject to a terminal disclaimer.

(21) Appl. No.: 11/547,975

(22) PCT Filed: Mar. 30, 2005

(86) PCT No.: PCT/EP2005/003294
§ 371 (c)(1),
(2), (4) Date: Dec. 20, 2007

(87) PCT Pub. No.: WO2005/097790
PCT Pub. Date: Oct. 20, 2005

(65) Prior Publication Data
US 2008/0139595 A1 Jun. 12, 2008

(30) Foreign Application Priority Data

Apr. 8, 2004 (DE) .......................... 10 2004 017 438

(51) Int. Cl.
*C07D 471/04* (2006.01)
*A61K 31/437* (2006.01)
(52) U.S. Cl. ....................................... 514/275; 544/324
(58) Field of Classification Search .................. 544/324; 514/275
See application file for complete search history.

(56) References Cited

U.S. PATENT DOCUMENTS

| 7,253,286 | B2 | 8/2007 | Funahashi et al. |
| 7,648,986 | B2 | 1/2010 | Nagarathnam et al. |
| 7,723,347 | B2 | 5/2010 | Schirok et al. |
| 7,737,153 | B2* | 6/2010 | Feurer et al. ............... 514/259.1 |
| 2001/0020030 | A1 | 9/2001 | Stewart et al. |
| 2003/0125344 | A1 | 7/2003 | Nagarathnam et al. |
| 2004/0014755 | A1 | 1/2004 | Nagarathnam et al. |
| 2005/0182040 | A1 | 8/2005 | Imazaki et al. |
| 2006/0004006 | A1 | 1/2006 | Borzilleri et al. |
| 2008/0249105 | A1 | 10/2008 | Bennabi et al. |

FOREIGN PATENT DOCUMENTS

| CA | 2489452 | 12/2003 |
| WO | 0222856 | 3/2002 |
| WO | 03062225 | 7/2003 |
| WO | 03062227 | 7/2003 |
| WO | 03106450 | 12/2003 |
| WO | 2004039796 | 5/2004 |

OTHER PUBLICATIONS

Vippagunta et al., Cyrstalline Solids, Advanced Drug Delivery Reviews, 48, pp. 3-26, 2001.*
Ulrich, Chapter 4: Crystallization, Kirk-Othmer Encyclopedia of Chemical Technology, Aug. 2002.*
West, Solid Solutions, Solid State Chemistry and its applications, pp. 358 & 365, 1988.*
Fukata et al., "Rho-Rho-kinase pathway in smooth muschle contraction and cytoskeletal reorganization of non-muscle cells," Trands in Pharmacological Sciences, 2001, 22:32-39.
Somlyo et al., "Cell calcium and its regulation in smooth muscle," FASEB J., 1989, 3:2266-2276.
Kamm et al., "The function of myosin and myosin light chain kinase phosphorylation in smooth muscle," Am Rev Pharmacol Toxicol, 1985, 25: 593-620.
Noda et al., "Involvement of rho in GTP-gamma-S-induced enhancement of phosporilation of 20kDa myosin light chain in vascular smooth muscle cells: inhibition of phosphatase activity," FEBS Letters, 1995, 367:246-250.
Uehata et al., "Calcium sensitization of smooth muscle mediated by a Rho-associated protein kinase in hypertension," Nature, Oct. 30, 1997, 389:990-994.
Somlyo et al., "Rho-Kinase inhibitor retards migration and in vivo dissemination of human prostate cancer cells," Biochemical and Biophysical Research Communications, 2000, 269:652-659.
U.S. Appl. No. 10/582,184, filed Sep. 26, 2007.

* cited by examiner

*Primary Examiner* — Deepak Rao
(74) *Attorney, Agent, or Firm* — Karen B. King; Jonathan R. Harris

(57) ABSTRACT

The invention relates to hetaryloxy-substituted phenylaminopyrimidines, to a process for their preparation and to their use for preparing medicaments for the treatment and/or prophylaxis of diseases in humans and animals, in particular cardiovascular disorders.

8 Claims, No Drawings

HETARYLOXY-SUBSTITUTED PHENYLAMINO PYRIMIDINES AS RHO KINASE INHIBITORS

The invention relates to hetaryloxy-substituted phenylaminopyrimidines, to a process for their preparation and to their use for preparing medicaments for the treatment and/or prophylaxis of diseases in humans and animals, in particular cardiovascular disorders.

An increase in the intracellular calcium concentration is one of the main factors triggering the contraction of the vascular musculature (Somlyo, A. P. and Himpens, B. *FASEB J.* 1989, 3, 2266-2276). This is effected primarily by agonists, such as, for example, phenylephrine or thromboxane A2 which, after stimulation of the phosphatidylinositol cascade, cause the release of calcium from the sarcoplasmatic reticulum. The elevated intracellular calcium activates the MLC kinase (myosin light-chain kinase) which phosphorylates the MLC subunits of the myosin molecule (Kamm, K. H. and Stull, J. T., *Annu. Rev. Pharmacol. Toxicol.* 1985, 25, 593-603). MLC phosphorylation induces the contraction of smooth muscles, MLC dephosphorylation after reduction of the intracellular calcium concentration results in the relaxation of the vessel.

In addition to the calcium-dependent MLC phosphorylation, there is a further, central but calcium-independent, regulation mechanism of the vascular tone. This is the Rho/Rho kinase signal path (Noda, M. et al., *FEBS Lett.* 1995, 367, 246-250; Uehata, M. et al., *Nature* 1997, 389, 990-994; Fukata, Y. et al., *Trends in Pharmacological Sciences* 2001, 22, 32-39). The binding of agonists such as, for example, phenylephrine or thromboxane A2 to their receptors results in the activation of the small G-proteins Rho which then interact with and activate Rho kinase. The activated Rho kinase inhibits myosin phosphatase following phosphorylation of a subunit of the enzyme. At the same time, Rho kinase phosphorylates MLC at the position which is also phosphorylated by MLC kinase. Inhibition of myosin phosphatase and phosphorylation of MLC induces the vascular musculature to contract. In contrast, inhibition of Rho kinase leads to a relaxation of the vessels. Accordingly, inhibitors of Rho kinase lower the blood pressure and increase coronary-perfusion.

In addition, inhibitors of Rho kinase cause inhibition of growth of tumor cells and metastases (Itoh et al. *Nat. Med.* 1999, 5, 221; Somlyo et al. *Biochem. Biophys. Res. Commun.* 2000, 269, 652) and inhibit angiogenesis (Uchida et al. *Biochem. Biophys. Res. Commun.* 2000, 269, 633; Gingras et al. *Biochem. J.* 2000, 348 Vol. 2, 273).

Structures similar to the compounds according to the invention are known from other indications. Thus, for example, US 2001/0020030 A1 discloses substituted thienopyridines and thieno-pyrimidines for the treatment of inflammatory disorders, WO 02/32872 discloses nitrogenous aromatic cyclic compounds as inhibitors of neovascularization.

Structures similar to the compounds according to the invention are furthermore described in WO 03/062225, WO 03/062227, WO 03/106450 and WO 04/039796 as Rho kinase inhibitors for the treatment of cancer and cardiovascular disorders. However, it has been found that these compounds, with respect to their in vivo properties, such as, for example, their action in the liver, their pharmacological action and their metabolic path, have disadvantages.

Accordingly, it was an object of the present invention to provide further hetaryloxy-substituted phenylaminopyrimidines which act as Rho kinase inhibitors, but which do not have the abovementioned disadvantages of the prior art.

The present invention provides compounds of the formula

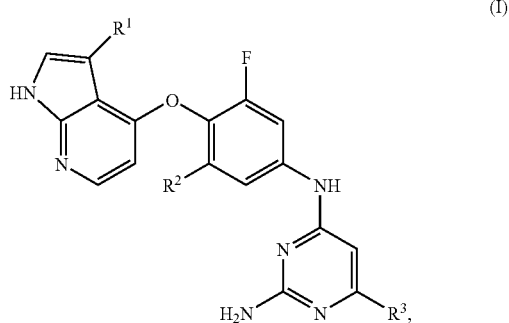

(I)

in which
$R^1$ represents chlorine, bromine, cyano, methyl, ethyl, hydroxyethyl, methoxyethyl or cyclopropyl,
$R^2$ represents hydrogen or fluorine,
$R^3$ represents hydrogen, chlorine, trifluoromethyl or pentafluoroethyl,
and their salts, hydrates, hydrates of the salts and solvates.

Compounds according to the invention are the compounds of the formula (I) and their salts, solvates and solvates of the salts; the compounds of the formulae given below embraced by formula (I) and their salts, solvates and solvates of the salts and the compounds given below as embodiments and embraced by formula (I) and their salts, solvates and solvates of the salts, if the compounds given below and embraced by formula (I) are not already salts, solvates and solvates of the salts.

Depending on their structure, some of the compounds according to the invention can exist in stereoisomeric form (enantiomers, diastereomers). Accordingly, the invention relates to the enantiomers or diastereomers and to their respective mixtures. The stereoisomerically uniform components can be isolated in a known manner from such mixtures of enantiomers and/or diastereomers.

Insofar as the compounds according to the invention may occur in the tautomeric form, the present invention embraces all tautomeric forms.

In the context of the present invention, preferred salts are physiologically acceptable salts of the compounds according to the invention. Also included, however, are salts which for their part are not suitable for pharmaceutical applications but which can be used, for example, for isolating or purifying the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are those forms of the compounds according to the invention which, in solid or liquid state, form a complex by coordination with solvent molecules. Hydrates are a specific form of solvates where the coordination is with water.

Preference is given to compounds of the formula (I) in which
$R^1$ represents chlorine, cyano, methyl, ethyl, hydroxyethyl, methoxyethyl or cyclopropyl,
$R^2$ represents hydrogen or fluorine,
$R^3$ represents hydrogen, chlorine, trifluoromethyl or pentafluoroethyl,
and their salts, hydrates, hydrates of the salts and solvates.

Preference is also given to compounds of the formula (I) in which
$R^1$ represents chlorine, cyano, methyl, ethyl, hydroxyethyl, methoxyethyl or cyclopropyl,
$R^2$ represents hydrogen or fluorine,
$R^3$ represents hydrogen, chlorine or trifluoromethyl,
and their salts, hydrates, hydrates of the salts and solvates.

Particular preference is given to compounds of the formula (I) in which
$R^1$ represents cyano, methyl or hydroxyethyl,
$R^2$ represents hydrogen or fluorine,
$R^3$ represents chlorine or trifluoromethyl,
and their salts, hydrates, hydrates of the salts and solvates.

The present invention furthermore provides a process for preparing the compounds of the formula (I), which is characterized in that
compounds of the formula (II)

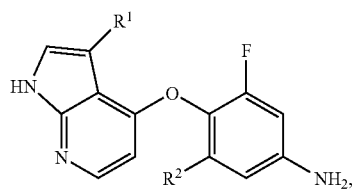

(II)

in which
$R^1$ and $R^2$ are as defined above
are reacted with compounds of the formula (III)

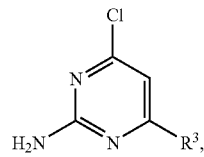

(III)

in which
$R^3$ is as defined above.

The reaction is generally carried out in aqueous hydrochloric acid solution, preferably in a temperature range of from 70° C. to 110° C., at atmospheric pressure.

To prepare compounds of the formula (II), for example, further radicals $R^1$ are introduced into compounds of the formula (IV)

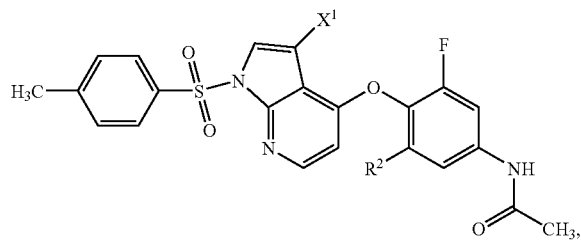

(IV)

in which
$R^2$ is as defined above and
$X^1$ represents halogen, preferably bromine or chlorine,
via organometallic reactions, such as, for example, Suzuki or Negishi reactions, or other palladium-catalyzed reactions known to the person skilled in the art. The synthesis routes for the various radicals $R^1$ are described in detail in the examples in the experimental part. The acyl and tosylate protective groups are subsequently removed using customary methods known to the person skilled in the art.

To prepare the compounds of the formula (IV), for example, compounds of the formula (V)

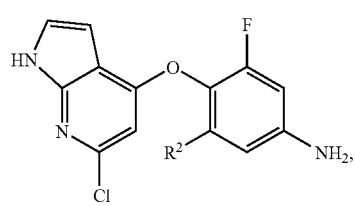

(V)

in which
$R^2$ is as defined above
are hydrogenated in a first step with palladium-on-carbon in ethanol at 50° C. under a hydrogen pressure of 2 bar, to remove the chlorine substituent.

In a second step, an acetyl protective group is introduced at the aniline by reaction with acetyl chloride in dichloromethane in the presence of triethylamine in a temperature range of from 0° C. to room temperature, at atmospheric pressure.

In a third step, the radical $X^1$ is then introduced:

in the case of $X^1$=bromine, the reaction is carried out in a mixture of glacial acetic acid and dichloromethane by adding bromine in a temperature range of from −10° C. to 10° C., at atmospheric pressure.

In the case of $X^1$=chlorine, the reaction is carried out using N-chlorosuccinimide in THF by addition of aqueous hydrochloric acid in a temperature range of from room temperature to the 15, reflux of the solvent, at atmospheric pressure.

In a subsequent fourth step, the tosylate protective group is introduced at the pyrrole nitrogen of the pyrrolopyridine by deprotonation with butyllithium solution in THF in a temperature range of from −78° C. to −50° C. at atmospheric pressure and subsequent reaction with toluenesulfonyl chloride in THF with warming to room temperature.

To prepare the compounds of the formula (V), for example, compounds of the formula (VI)

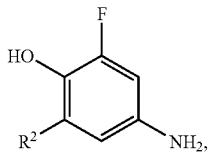

(VI)

in which
$R^2$ is as defined above

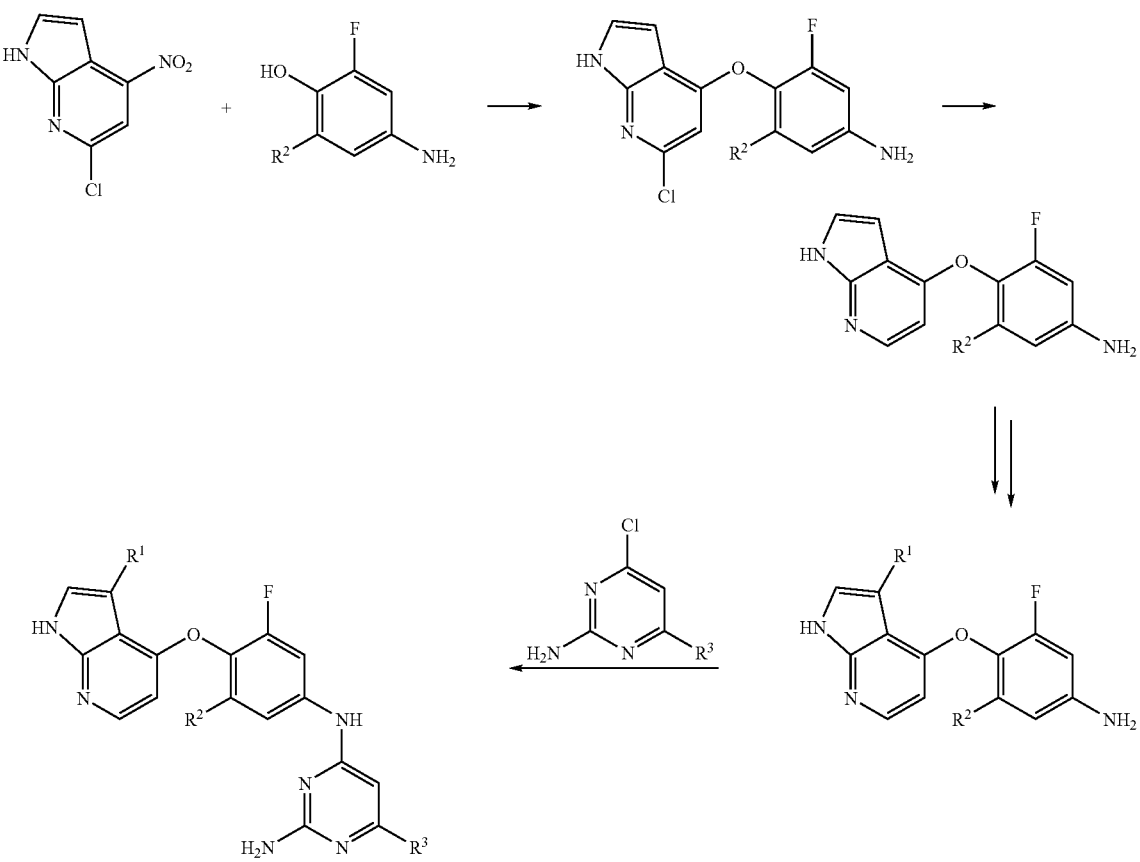

are reacted with the compound of the formula (VII)

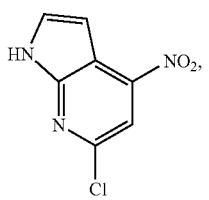

(VII)

The reaction is carried out without solvent in the presence of potassium hydroxide as base in the melt at a temperature of from 200° C. to 280° C. or, preferably, in an inert solvent, such as, for example, N,N-dimethylformamide, N-methylpyrrolidone, dimethylsulfoxide or nitrobenzene, in the presence of a base, such as, for example, potassium carbonate, potassium hydroxide, potassium tert-butoxide or sodium hydride, at a temperature of from 120° C. to 280° C.

The compounds of the formulae (III), (VI) and (VII) are known per se to the person skilled in the art or can be prepared by customary processes known from the literature.

The preparation of the compounds according to the invention can be illustrated by the synthesis scheme below.

The compounds according to the invention have an unforeseeable useful spectrum of pharmacological and pharmacokinetic action.

Accordingly, they are suitable for use as pharmaceuticals for the treatment and/or prophylaxis of diseases in humans and animals.

The pharmaceutical activity of the compounds according to the invention can be explained by their action as Rho kinase inhibitors.

The present invention also provides the use of the compounds according to the invention for the treatment of and/or prophylaxis of disorders, preferably cardiovascular disorders.

The compounds according to the invention are suitable for the prophylaxis and/or treatment of cardiovascular disorders such as, for example, hypertension and cardiac insufficiency, stable and unstable angina pectoris, disorders of peripheral and cardiac vessels, of arrhythmias, of thrombolic disorders and ischemias, such as myocardial infarction, stroke, transitory and ischemic attacks, obstruction of peripheral circulation, subarachnoidal hemorrhages, prevention of restenoses, such as, for example, after thrombolysis therapies, percutaneous transluminal angioplasties (PTA) percutaneous transluminal coronary angioplasties (PTCA), bypass, and for the prophylaxis and/or treatment of arteriosclerosis, Alzheimer's disease, kidney failure, glaucoma, asthmatic disorders, COPD and diseases of the urogenital system, such as, for example, prostate hypertrophy, erectile dysfunction, female sexual dysfunction, osteoporosis, gastroparesis and incontinence.

The compounds according to the invention can furthermore be used for the prophylaxis and/or treatment of cancers, in particular of tumors.

In the context of the present invention, the definition of tumors includes both benign and malignant tumors and thus, for example, also benign neoplasias, dysplasias, hyperplasias, and neoplasias with metastasis formation. Further examples of tumors are carcinomas, sarcomas, carcincosarcomas, tumors of the hemopoietic organs, tumors of the nervous tissue, for example of the brain, or tumors of skin cells. In tumor formation, uncontrolled or inadequately controlled cell division occurs. The tumor can be locally restricted, but it can also infiltrate the surrounding tissue and then get lodged by the lymphatic system or by the bloodstream in a new location. There are thus primary and secondary tumors. Primary tumors are originally formed in the organ in which they are found. Secondary tumors have been lodged in another organ by metastasis formation and then spread in their new location.

The present invention also provides the use of the compounds according to the invention for the prophylaxis and/or treatment of disorders, in particular the syndromes mentioned above.

The present invention also provides the use of the compounds according to the invention for preparing medicaments for the prophylaxis and/or treatment of disorders, in particular the syndromes mentioned above.

The present invention also provides a method for the prophylaxis and/or treatment of disorders, in particular the disorders mentioned above, using a cardiovascularly effective amount of the compound according to the invention.

The present invention also provides medicaments, comprising a compound according to the invention in combination with one or more further active compounds, in particular for the prophylaxis and/or treatment of the disorders mentioned above.

The compound according to the invention can act systemically and/or locally. For this purpose, it can be administered in a suitable manner, such as, for example, orally, parenterally, pulmonarily, nasally, sublingually, lingually, buccally, rectally, transdermally, conjunctivally, otically, as stents or as an implant.

For these administration routes, the compound according to the invention can be administered in suitable administration forms.

Suitable for oral administration are administration forms working according to the prior art, which release the compounds according to the invention rapidly and/or in modified form and which contain the compounds according to the invention in crystalline and/or amorphized and/or dissolved form, such as, for example, tablets (non-coated or coated tablets, for example coated with enteric, slowly dissolving or insoluble coats which control the release of the compounds according to the invention), tablets which decompose rapidly in the oral cavity or films/wafers, capsules, sugarcoated tablets, granules, pellets, powders, emulsions, suspensions, aerosols or solutions.

Parenteral administration can take place with circumvention of an absorption step (intravenous, intraarterial, intracardiac, intraspinal or intralumbar) or with involvement of an absorption (intramuscular, subcutaneous, intracutaneous, percutaneous or intraperitoneal). For parenteral administration, suitable administration forms are, inter alia, injection and infusion preparations in the form of solutions, suspensions, emulsions, lyophilisates and sterile powders.

Suitable for the other administration routes are, for example, pharmaceutical forms for inhalation (inter alia powder inhalers, nebulizers), nasal drops/solutions, sprays; tablets or capsules to be administered lingually, sublingually or buccally, suppositories, ear and eye preparations, vaginal capsules, aqueous suspensions (lotions, shake lotions), lipophilic suspensions, ointments, creams, milk, pastes, dusting powder, stents or implants.

The compounds according to the invention can be converted into the administration forms mentioned in a manner known per se. This takes place using inert nontoxic, pharmaceutically acceptable auxiliaries. These include, inter alia, carriers (for example microcrystalline cellulose), solvents (for example liquid polyethylene glycols), emulsifiers (for example sodium dodecylsulfate), dispersants (for example polyvinylpyrrolidone), synthetic and natural biopolymers (for example albumin), stabilizers (for example antioxidants, such as ascorbic acid), colorants (for example inorganic pigments, such as iron oxides) or taste and/or odor corrigens.

The present invention also provides medicaments comprising at least one compound according to the invention, preferably together with one or more inert nontoxic, pharmaceutically acceptable auxiliaries, and their use for the purposes mentioned above.

In general, it has been found to be advantageous both in human and in veterinary medicine to administer the compound according to the invention in total amounts of from about 0.01 to about 700, preferably 0.01 to 100, mg/kg of body weight per 24 hours, if appropriate in the form of a plurality of individual doses, to obtain the desired results. An individual dose contains the compound according to the invention preferably in amounts of from about 0.1 to about 80, in particular 0.1 to 30, mg/kg of body weight.

In spite of this, it may be necessary, if appropriate, to deviate from the amounts mentioned, namely depending on the body weight, the route of administration, the individual response to the active compound, the type of preparation and the time or interval at which administration takes place. Thus, in some cases it may be sufficient to use less than the above-mentioned minimum amount, whereas in other cases the upper limit mentioned has to be exceeded. In the case of the administration of relatively large amounts, it may be advisable to divide these into several individual administrations over the course of the day.

The percentages in the tests and examples below are, unless indicated otherwise, percentages by weight; parts are parts by weight. Solvent ratios, dilution ratios and concentrations of liquid/liquid solutions are in each case based on the volume.

A. EXAMPLES

Abbreviations

TLC thin-layer chromatography
DCI direct chemical ionization (in MS)
DCM dichloromethane DIEA N,N-diisopropylethylamine
DMA dimethylacetamide
DMF N,N-dimethylformamide
DMSO dimethyl sulfoxide
EA ethyl acetate
EI electron impact ionization (in MS)
ESI electrospray ionization (in MS)
m.p. melting point
sat. saturated
h hour
HATU O-(7-azabenzotriazol-1-yl)-N,N,N',N'-tetramethyluronium hexafluorophosphate
HOAT 3H-[1,2,3]-triazol[4,5-b]pyridin-3-ole
HOBt 1-hydroxy-1H-benzotriazole×H$_2$O
HPLC high pressure, high performance liquid chromatography
conc. concentrated
LC-MS liquid chromatography-coupled mass spectroscopy
LDA lithium diisopropylamide
min minutes
MPLC medium pressure, medium performance liquid chromatography
MS mass spectroscopy
NMR nuclear magnetic resonance spectroscopy
org. organic
RF reflux
R$_f$ retention factor (in TLC)
RP-HPLC reverse phase HPLC
RT room temperature
R$_t$ retention time (in HPLC)
TFA trifluoroacetic acid
THF tetrahydrofuran
HPLC, LCMS and GCMS Methods:

Method 1 (LC/MS): MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2 (LC/MS): Instrument: Micromass Quattro LCZ with HPLC Agilent series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 208-400 nm.

Method 3 (LC/MS): MS instrument type: Micromass ZQ; HPLC instrument type: HP 1100 series; UV DAD; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 4 (HPLC): Instrument: HP 1100 with DAD detection; column: Kromasil 100 RP-18, 60 mm×2.1 mm, 3.5 μm; mobile phase A: 5 ml of perchloric acid (70% strength)/l of water, mobile phase B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; oven: 30° C.; UV detection: 210 nm.

Method 5 (LC-MS): Instrument: Micromass Platform LCZ with HPLC Agilent series 1100; column: Thermo HyPURITY Aquastar 3μ 50 mm×2.1 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; oven: 50° C.; flow rate: 0.8 ml/min; UV detection: 210 nm.

Method 6 (LC/MS): Instrument: Micromass Platform LCZ with HPLC Agilent series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Preparative HPLC: column: YMC Gel ODS-AQ S-5/15 μM, 250 mm×30 mm; mobile phase A: water, mobile phase B: acetonitrile; gradient: 0.00 min 30% B→3.00 min 30% B→34.0 min 95% B→38.0 min 30% B; temp.: room temperature; flow rate: 50 ml/min; UV detection.

Starting Materials

Example 1A

1H-Pyrrolo[2,3-b]pyridine 7-oide

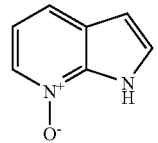

(Antonini, Ippolito; Claudi, Francesco; Cristalli, Gloria; Franchetti, Palmarisa; Grifantini, Mario; Martelli, Sante; *J. Med. Chem.* 1982, 25(10), 1258-1261) 540 g (2.35 mol) of 3-chloroperbenzoic acid are dissolved in 6.11 l of dichloromethane, and the water that separates off is removed. The organic phase is dried over sodium sulfate and cooled to 0° C. A solution of 163 g (1.38 mol) of 1H-pyrrolo[2,3-b]pyridine (Hands, D.; Bishop, B.; Cameron, M.; Edwards, T. S.; Cottrell, I. F.; Wright, S. H. B.; *Synthesis* 1996 (7), 877-882) in 1.00 l of dichloromethane is then added, and the temperature is allowed to rise to room temperature. After 2 hours, such an amount of methanol is added that the precipitate formed redissolves. The mixture is filtered through silica gel (mobile phase: dichloromethane/methanol 95:5). After concentration, the product fractions are dried under high vacuum.

Yield: 145 g (75% of theory)

HPLC (Method 4): R$_t$=2.02 min.

MS (ESI pos.): m/z=135 (M+H)$^+$, 152 (M+NH$_4$)$^+$, 269 (2M+H)$^+$.

$^1$H-NMR (DMSO-d$_6$, 200 MHz): δ=6.58 (d, 1H), 7.07 (dd, 1H), 7.48 (d, 1H), 7.65 (d, 1H), 8.17 (d, 1H), 12.42-12.64 (br. s, 1H).

Example 2A

4-Nitro-1H-pyrrolo[2,3-b]pyridine 7-oxide

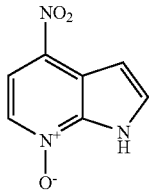

Based on the results of the differential thermoanalysis, it is not recommended to carry out reactions on a scale larger than five times the amount of the size described.

A solution of 20.0 g (149 mmol) of 1H-pyrrolo[2,3-b]pyridine 7-oxide in 160 ml of trifluoroacetic acid is cooled to room temperature. 69.3 ml of 65% strength nitric acid are then slowly added dropwise, and the mixture is allowed to stir at room temperature for 2 hours. The mixture is poured onto ice, and the pH is adjusted to 8-9 using 45% strength sodium hydroxide solution. The precipitate is filtered off with suction and washed with water. The crude products of 4 batches of the size described and a 13 g batch carried out analogously are combined and purified together. The crude products are suspended in water, and the pH is adjusted to 8-9 using, 2N sodium hydroxide solution. After 10 min of stirring, the precipitate is filtered off with suction and dried under high vacuum. (Schneller, Stewart W.; Luo, Jiann-Kuan; *J. Org. Chem.* 1980, 45, 4045-4048.)

Yield: 29.7 g (24% of theory)

HPLC (Method 4): $R_t$=3.02 min.

MS (ESI pos.): m/z=180 (M+H)$^+$, 197 (M+NH$_4$)$^+$, 359 (2M+H)$^+$.

$^1$H-NMR (DMSO-d$_6$, 200 MHz): δ=7.03 (d, 1H), 7.80 (d, 1H), 8.03 (d, 1H), 8.31 (d, 1H), 13.22-13.41 (br. s, 1H).

Example 3A

6-Chloro-4-nitro-1H-pyrrolo[2,3-b]pyridine

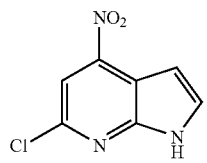

Under an atmosphere of argon, 5.00 g (27.9 mmol) of 4-nitro-1H-pyrrolo[2,3-b]pyridine 7-oxide and 11.8 ml (55.8 mmol) of hexamethyldisilazane are initially charged in 290 ml of THF. At RT, 10.8 ml (140 mmol) of methyl chloroformate are added. The solution is stirred at RT overnight. The reaction solution is filtered through a silica gel cartridge, and the cartridge is washed with dichloromethane/methanol 10:1.

Yield: 2.8 g (70% of theory)

LC-MS (Method 3): $R_t$=2.15 min.

MS (ESI pos.): m/z=198 (M+H)$^+$.

$^1$H-NMR (DMSO-d$_6$, 200 MHz): δ=7.00 (mc, 1H), 7.97 (s, 1H), 8.00 (t, 1H), 12.79 (s, 1H).

Example 4A

4-[(6-Chloro-1H-pyrrolo[2,3-b]pyridin-4-yl)oxy]-3,5-difluoroaniline

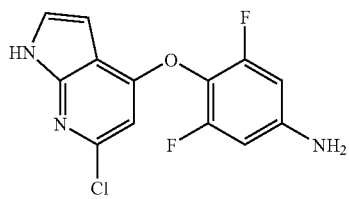

664 mg (3.36 mmol) of 6-chloro-4-nitro-1H-pyrrolo[2,3-b]pyridine, 1.39 g (10.1 mmol) of powdered potassium carbonate and 877 mg (5.04 mmol) of sodium dithionite are suspended in 10 ml of DMSO. The mixture is degassed, and 915 mg (5.04 mmol) of 4-amino-2,6-difluorophenol hydrochloride are added. The mixture is heated at 120° C. for 4 hours. After addition of ethyl acetate, the mixture is filtered off with suction through celite, and the celite is washed with ethyl acetate. The filtrate is shaken three times with saturated sodium bicarbonate solution and with saturated, sodium chloride solution. The filtrate is dried over sodium sulfate and the solvent is removed under reduced pressure. The residue is purified by column chromatography (silica gel 60, mobile phase: dichloromethane/methanol=50:1).

Yield: 356 mg (36% of theory)

LC-MS (Method 1): $R_t$=2.05 min.

MS (ESI pos.): m/z=296 (M+H)$^+$.

$^1$H-NMR (DMSO-d$_6$, 400 MHz): δ=5.84 (s, 2H), 6.28 (mc, 1H), 6.38-6.41 (m, 3H), 7.42 (mc, 1H), 12.02 (s, 1H).

Example 5A

3,5-Difluoro-4-1H-pyrrolo[2,3-b]pyridin-4-yloxy)aniline

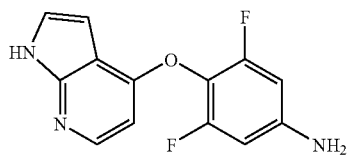

Analogously to 3-fluoro-4-(1H-pyrrolo[2,3-b]pyridin-4-yloxy)aniline, the title compound is obtained by catalytic hydrogenation of 408 mg (1.38 mmol) of 4-[(6-chloro-1H-pyrrolo[2,3-b]pyridin-4-yl)oxy]-3,5-difluoraniline.

Yield: 360 mg (100% of theory)

LC-MS (Method 1): $R_t$=1.46 min.

MS (ESI pos.): m/z=262 (M+H)$^+$.

$^1$H-NMR (DMSO-$d_6$, 400 MHz): δ=5.77 (br. s, 1H), 6.28 (dd, 1H), 6.34-6.40 (m, 3H), 7.37 (dd, 1H), 8.06 (d, 1H), 11.76 (br. s, 1H).

Example 6A

N-[3,5-Difluoro-4-(1H-pyrrolo[2,3-b]pyridin-4-yloxy)phenyl]acetamide

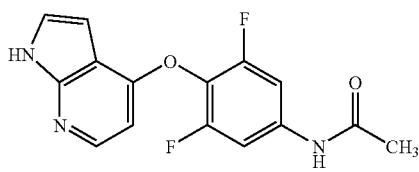

1.60 g (6.14 mmol) of 3,5-difluoro-4-(1H-pyrrolo[2,3-b]pyridin-4-yloxy)aniline are suspended in 45 ml of dichloromethane and cooled to 0° C. 2.57 ml (18.4 mmol) of triethylamine and 0.87 ml (12.3 mmol) of acetyl chloride are added dropwise, and stirring at 0° C. is continued for 2.5 hours. A further 0.86 ml (6.14 mmol) of triethylamine and 0.44 ml (6.14 mmol) of acetyl chloride are added, and the mixture is allowed to react for another hour. Saturated sodium bicarbonate solution is then added, and the mixture is stirred at RT for 10 min. The mixture is extracted twice with dichloromethane. The combined organic phases are dried over magnesium sulfate and the solvent is removed under reduced pressure. The crude product is taken up in 45 ml of ethanol. 1.14 ml (6.14 mmol) of 5.4M sodium methoxide solution are added, and the mixture is stirred at RT for 30 min. The mixture is concentrated and the product is purified by chromatography on silica gel (mobile phase: dichloromethane/methanol (7N ammonia) 100:1 to 100:5).

Yield: 1.05 g (56% of theory)
LC-MS (Method 2): $R_t$=1.76 min.
MS (ESI pos.): m/z 304 (M+H)$^+$.
$^1$H-NMR (DMSO-$d_6$, 400 MHz): δ=2.10 (s, 3H), 6.28 (dd, 1H), 6.41 (d, 1H), 7.41 (dd, 1H), 7.53 (m, 2H), 8.08 (d, 1H), 10.40 (s, 1H), 11.83 (br. s, 1H).

Example 7A

N-{4-[(3-Bromo-1H-pyrrolo[2,3-b]pyridin-4-yl)oxy]-3,5-difluorophenyl}acetamide

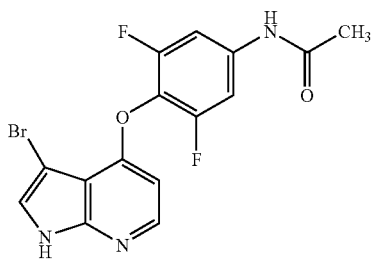

1.05 g (3.45 mmol) of N-[3,5-difluoro-4-(1H-pyrrolo[2,3-b]pyridin-4-yloxy)phenyl]acetamide are dissolved in 35 ml of glacial acetic acid and, using an ice bath, cooled to about 10° C. 4.8 ml (4.8 mmol) of a 1M solution of bromine in dichloromethane are added, and the mixture is stirred at 20° C. for about 30 min, resulting in the precipitation of a solid. The solid is filtered off with suction and washed with ethyl acetate. The mother liquor is neutralized using conc. aqueous sodium hydroxide solution and extracted with ethyl acetate. The crystals that were filtered off with suction are dissolved in 3 ml of DMF. The mixture is diluted with ethyl acetate and extracted three times with 1N sodium hydroxide solution. The combined organic phases are dried over magnesium sulfate. The solvent is removed under reduced pressure. The product is reacted without further purification.

Yield: 1.32 g (100% of theory)
LC-MS (Method 2): $R_t$=2.10 min.
MS (ESI pos.): m/z=382, 384 (M+H)$^+$.
$^1$H-NMR (DMSO-$d_6$, 400 MHz): δ=2.10 (s, 3H), 6.33 (d, 1H), 7.55 (d, 2H), 7.65 (d, 1H), 8.10 (d, 1H), 10.43 (s, 1H), 12.22 (br. s, 1H).

Example 8A

N-[4-({3-Bromo-1-[(4-methylphenyl)sulfonyl]-1H-pyrrolo[2,3-b]pyridin-4-yl}oxy)-3,5-difluorophenyl]acetamide

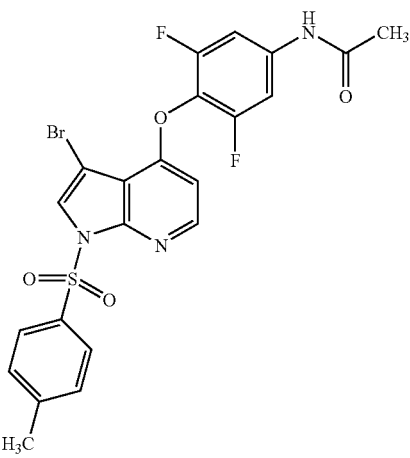

1.37 g (3.58 mmol) of N-{4-[(3-bromo-1H-pyrrolo[2,3-b]pyridin-4-yl)oxy]-3,5-difluorophenyl}acetamide are dissolved in 200 ml of THF and cooled to −78° C. 1.6 ml (4.0 mmol) of a 2.5M n-butyllithium solution are added dropwise, and the mixture is stirred for 15 min. 752 mg (3.94 mmol) of p-toluenesulfonyl chloride as a solution in 7.5 ml of THF are then added dropwise. The reaction solution is allowed to warm to RT and stirred for one hour. The mixture is then partitioned between ethyl acetate and 0.1N aqueous sodium hydroxide solution. The aqueous phase is extracted twice with ethyl acetate. The combined organic phases are dried over magnesium sulfate and the solvent is removed under reduced pressure. The product is purified by column chromatography on silica gel (mobile phase: dichloromethane/acetone 20:1 to 10:1).

Yield: 851 mg (44% of theory)
LC-MS (Method 1): $R_t$=2.61 min.
MS (ESI pos.): m/z=536, 538 (M+H)$^+$.

$^1$H-NMR (DMSO-d$_6$, 300 MHz): δ=2.09 (s, 3H), 2.36 (s, 3H), 6.64 (d, 1H), 7.45 (d, 2H), 7.50-7.57 (m, 2H), 8.03 (d, 2H), 8.13 (s, 1H), 8.25 (d, 1H), 10.40 (s, 1H).

Example 9A

N-[3,5-Difluoro-4-{3-methyl-1-[(4-methylphenyl)sulfonyl]-1H-pyrrolo[2,3-b]pyridin-4-yl}oxy)phenyl]acetamide

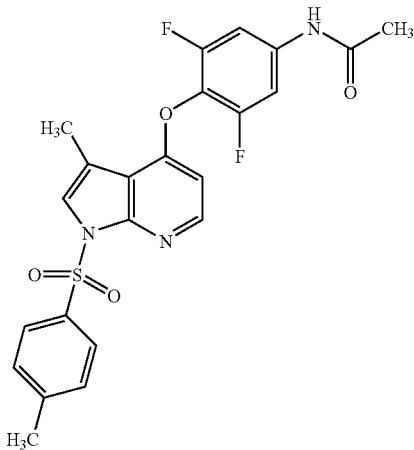

895 mg (1.67 mmol) of N-[4-{3-bromo-1-[(4-methylphenyl)sulfonyl]-1H-pyrrolo[2,3-b]pyridin-4-yl}oxy)-3,5-difluorophenyl]acetamide are dissolved in dioxane (20 ml). The mixture is degassed and vented with, argon. 2.5 ml (5.0 mmol) of a 2M solution of dimethyl zinc in toluene and 68 mg (0.08 mmol) of [1,1'-bis(diphenylphosphino)ferrocene]palladium(II) chloride/methylene dichloride complex are added, and the mixture is heated at 100° C. for 2 hours. The mixture is allowed to cool to RT, ethyl acetate and 1M hydrochloric acid are added and the aqueous phase is extracted with ethyl acetate. The combined organic phases are dried over sodium sulfate and the solvent is removed under reduced pressure. The residue is purified by column chromatography on silica gel (mobile phase: dichloromethane/acetone 20:1 to 10:1).

Yield: 702 mg (89% of theory)
LC-MS (Method 1): R$_t$=2.49 min.
MS (ESI pos.): m/z=472 (M+H)$^+$.
$^1$H-NMR (DMSO-d$_6$, 400 MHz): δ=2.09 (s, 3H), 2.35 (s, 3H), 2.41 (s, 3H), 6.52 (d, 1H), 7.42 (d, 2H), 7.52 (m, 2H), 7.66 (s, 1H), 7.97 (d, 2H), 8.17 (d, 1H), 10.43 (s, 1H).

Example 10A 3,5-Difluoro-4-[(3-methyl-1H-pyrrolo[2,3-b]pyridin-4-yl)oxy]aniline

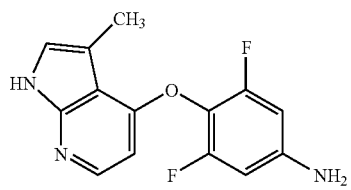

690 mg (1.46 mmol) of N-[3,5-difluoro-4-({3-methyl-1-[(4-methylphenyl)sulfonyl]-1H-pyrrolo[2,3-b]pyridin-4-yl}oxy)phenyl]acetamide are dissolved in 25 ml of ethanol. 12.5 ml of 20% strength aqueous sodium hydroxide solution are added, and the reaction mixture is heated at 90° C. for 4.5 hours. The reaction solution is partitioned between ethyl acetate and water. The aqueous phase is extracted with ethyl acetate. The combined organic phases are dried over magnesium sulfate and the solvent is removed under reduced pressure. The product is reacted without further purification.

Yield: 402 mg (100% of theory)
LC-MS (Method 1): R$_t$=1.53 min.
MS (ESI pos.): m/z=276 (M+H)$^+$. —H-NMR (DMSO-d$_6$, 300 MHz): δ=2.42 (s, 3H), 5.72 (br. s, 2H), 6.15 (d, 1H), 6.33-6.45 (m, 2H), 7.11 (s, 1H), 7.97 (d, 1H), 11.32 (br. s, 1H).

Example 11A 2,2,2-Trifluoro-N-[3,5-difluoro-4-(1H-pyrrolo[2,3-b]pyridin-4-ylox)phenyl]acetamide

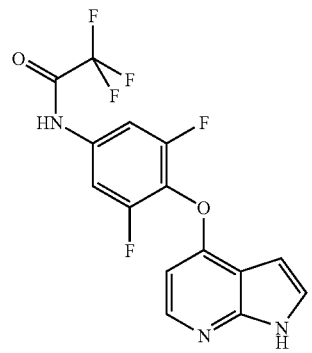

At 0° C., 0.16 ml (1.14 mmol) of trifluoroacetic anhydride are added dropwise to a solution of 200 mg (0.76 mmol) of 3,5-difluoro-4-(1H-pyrrolo[2,3-b]pyridin-4-yloxy)aniline and 0.21 ml (1.53 mmol) of triethylamine in anhydrous dichloromethane. The mixture is stirred at 0° C. for 20 min and the reaction is terminated by dropwise addition of a saturated sodium bicarbonate solution (10 ml). The suspension is allowed to warm to RT and the phases are separated. The aqueous phase is extracted with tert-butyl methyl ether (10 ml). The combined organic phases are washed with a saturated sodium chloride solution. The organic solution is dried over magnesium sulfate and concentrated. This gives a solid which is not purified any further.

Yield: 270 mg (98% of theory)
HPLC (Method 3): R$_t$=2.21 min.
MS (ESI pos.): m/z=358 (M+H)$^+$.

Example 12A

N-{4-[(3-Chloro-1H-pyrrolo[2,3-b]pyridin-4-yl)oxy]-3,5-difluorophenyl}-2,2,2-trifluoroacetamide

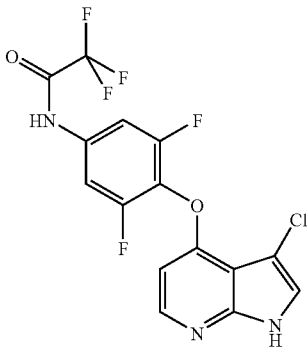

204 mg (1.54 mmol) of N-chlorosuccinimide and 50 µl of 1M aqueous hydrochloric acid are added to a solution of 250 mg (0.70 mmol) of 2,2,2-trifluoro-N-[3,5-difluoro-4-(1H-pyrrolo[2,3-b]pyridin-4-yloxy)phenyl]acetamide in anhydrous tetrahydrofuran (5 ml). The solution is stirred at RT overnight. The title compound precipitates from the reaction mixture. A solid is obtained by filtration with suction and drying.

Yield: 90 mg (33% of theory)

HPLC (Method 3): $R_t$=2.45 min.

MS (ESI pos.): m/z=392, 394 (M+H)$^+$.

Example 13A

4-[(3-Chloro-1H-pyrrolo[2,3-b]pyridin-4-yl)oxy]-3,5-difluoroaniline

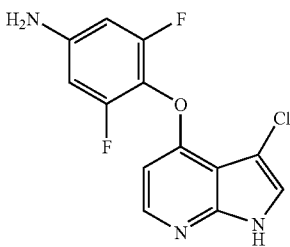

3 ml of a 1N sodium hydroxide solution are added to a solution of 90 mg (0.23 mmol) of N-{4-[(3-chloro-1H-pyrrolo[2,3-b]pyridin-4-yl)oxy]-3,5-difluorophenyl}-2,2,2-trifluoroacetamide in ethanol (5 ml). The reaction is stirred overnight. The solution is extracted with tert-butyl methyl ether (two times 10 ml). The combined organic phases are washed with a saturated sodium chloride solution. The organic phase is dried over magnesium sulfate and concentrated. This gives a solid which is not purified any further.

Yield: 65 mg (96% of theory)

HPLC (Method 2): $R_t$=2.13 min.

MS (ESI pos.): m/z=296, 298 (M+H)$^+$.

Example 14A

4-[(6-Chloro-1H-pyrrolo[2,3-b]pyridin-4-yl)oxy]-3-fluoroaniline

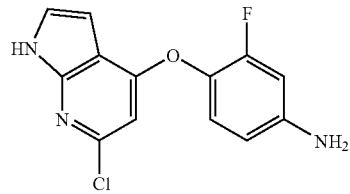

0.77 g (6.07 mmol) of 4-amino-2-fluorophenol is dissolved in DMF. 0.68 g (6.07 mmol) of potassium tert-butoxide is added, and the mixture is stirred at room temperature for 30 minutes. 0.35 g (2.53 mmol) of powdered potassium carbonate and 1.00 g (5.06 mmol) of 6-chloro-4-nitro-1H-pyrrolo[2,3-b]pyridine are then added successively. The mixture is stirred at 120° C. for 12 hours. After cooling, the mixture is diluted with ethyl acetate (200 ml). The suspension is filtered off with suction through Celite®, and the celite is washed with ethyl acetate. The solution is extracted successively with aqueous sodium bicarbonate solution and sodium chloride solution. The organic phase is dried over anhydrous magnesium sulfate and concentrated. The residue is purified by column chromatography (silica gel 60, mobile phase: dichloromethane/acetone 5:1).

Yield: 0.95 g (67% of theory)

Alternative Preparation Method:

A mixture of 1.80 g (9.11 mmol) of 6-chloro-4-nitro-1H-pyrrolo[2,3-b]pyridine, 3.78 g (27.3 mmol) of potassium carbonate and 3.17 g (18.2 mmol) of sodium dithionite in 26 ml of DMSO is degassed. 2.32 g (18.2 mmol) of 4-amino-2-fluorophenol are added, and the mixture is heated at 120° C. for 4 hours. The mixture is then diluted with ethyl acetate and filtered off with suction through Celite®. The filtrate is washed twice with sodium carbonate and once with sodium chloride solution, dried over sodium sulfate and concentrated. The product is purified by column chromatography on silica gel (mobile phase: dichloromethane/methanol 100:2).

LC-MS (Method 2): $R_t$=2.09 min.

MS (ESIpos): m/z=278 (M+H)$^+$.

$^1$H-NMR (DMSO-d$_6$, 200 MHz): δ=5.52 (br. s, 2H), 6.21-6.30 (m, 2H), 6.44 (dd, 1H), 6.53 (dd, 1H), 7.07 (dd, 1H), 7.39 (dd, 1H), 1.1.96 (br. s, 1H).

Example 15A

3-Fluoro-4-(1H-pyrrolo[2,3-b]pyridin-4-yloxy)aniline

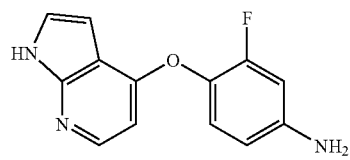

3.2 g (11.5 mmol) of 4-[(6-chloro-1H-pyrrolo[2,3-b]pyridin-4-yl)oxy]-3-fluoroaniline are dissolved in ethanol at 50° C. The solution is then allowed to cool to RT, and 2.45 g (2.30 mmol) of 10% palladium-on-carbon are added. The mixture is hydrogenated under a hydrogen pressure of 2 bar overnight. The mixture is, then filtered off with suction through kieselguhr, the kieselguhr is washed with ethanol and the filtrate is concentrated.

Yield: 2.5 g (89% of theory)

LC-MS (Method 1): $R_t$=1.18 min.

MS (ESI pos.): m/z=244 (M+H)$^+$.

$^1$H-NMR (DMSO-d$_6$, 200 MHz): δ=5.45 (mc, 2H), 6.25 (mc, 2H), 6.40-6.55 (br. 2H), 7.05 (t, 1H), 7.33 (mc, 1H), 8.25 (d, 1H), 11.69 (s, 1H).

Example 16A

N-[3-Fluoro-4-(1H-pyrrolo[2,3-b]pyridin-4-yloxy)phenyl]acetamide

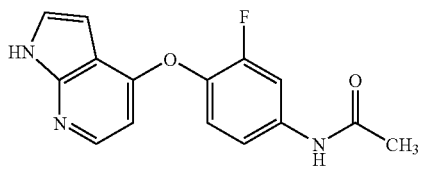

5.00 g (17.9 mmol) of 3-fluoro-4-(1H-pyrrolo[2,3-b]pyridin-4-yloxy)aniline hydrochloride are suspended in 100 ml of dichloromethane and cooled to 0° C. 9.97 ml (71.5 mmol) of triethylamine and 3.81 ml (53.6 mmol) of acetyl chloride are added dropwise, and the mixture is stirred at 0° C. for another 2 hours. Saturated sodium bicarbonate solution is added, and the mixture is stirred at RT for 10 min. The mixture is then extracted twice with dichloromethane. Insoluble components are dissolved using a little acetone, and the mixture is diluted with dichloromethane and washed with saturated sodium chloride solution. The combined organic phases are dried over magnesium sulfate and the solvent is removed under reduced pressure. The crude product is taken up in 100 ml of ethanol. 3.31 ml (17.9 mmol) of 5.4 M sodium methoxide solution are added, and the mixture is stirred at RT for 30 min. The mixture is concentrated and the product is purified by chromatography on silica gel (mobile phase: dichloromethane/methanol (7N ammonia) 100:1 to 100:5).

Yield: 3.92 g (77% of theory)

LC-MS (Method 3): $R_t$=1.56 min.

MS (ESI pos.): m/z 286 (M+H)$^+$.

$^1$H-NMR (DMSO-d$_6$, 300 MHz): δ=2.08 (s, 3H), 6.22 (dd, 1H), 6.35 (d, 1H), 7.28-7.38 (m, 3H), 7.80 (dd, 1H), 8.07 (d, 1H), 10.21 (br. s, 1H), 11.72 (br. s, 1H).

Example 17A

N-{4-[(3-Bromo-1H-pyrrolo[2,3-b]pyridin-4-yl)oxy]-3-fluorophenyl}acetamide

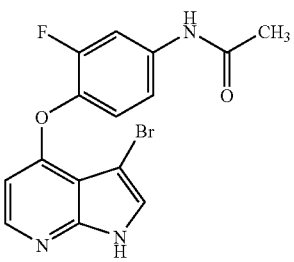

4.00 g (14.0 mmol) of [3-fluoro-4-(1H-pyrrolo[2,3-b]pyridin-4-yloxy)phenyl]acetamide are dissolved in 200 ml of glacial acetic acid and, using an ice bath, cooled to about 10° C. 21.0 ml (21.0 mmol) of a 1M solution of bromine in dichloromethane are added and the mixture is stirred at 10° C. for about 15 min, resulting the precipitation of a solid. The solid is filtered off with suction and washed with ethyl acetate. The crystals which were filtered off with suction are dissolved in 30 ml of DMF. The solution is diluted with 500 ml of ethyl acetate and extracted three times with 300 ml of 1M sodium hydroxide solution. The mixture is dried over magnesium sulfate and the solvent is removed under reduced pressure.

Yield: 3.44 g (66% of theory)

LC-MS (Method 6): $R_t$=2.03 min.

MS (ESI pos.): m/z=364, 366 (M+H)$^+$.

$^1$H-NMR (DMSO-d$_6$, 300 MHz): δ=2.08 (s, 3H), 6.27 (dd, 1H), 7.28-7.38 (m, 2H), 7.60 (d, 1H), 7.82 (dd, 1H), 8.09 (d, 1H), 10.21 (br. s, 1H), 12.11 (br. s, 1H).

Example 18A

3-Fluoro-4-({1-[(4-methylphenyl)sulfonyl]-1H-pyrrolo[2,3-b]pyridin-4-yl}oxy)aniline

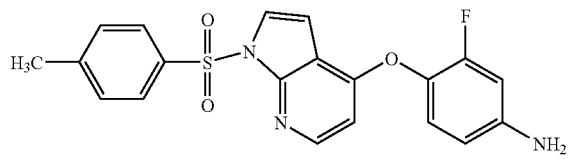

998 mg (4.10 mmol) of 3-fluoro-4-1H-pyrrolo[2,3-b]pyridin-4-yloxy)aniline are dissolved in 50 ml of THF, 230 mg (5.74 mmol) of sodium hydride (in THF) are added and the mixture is then stirred at RT for one hour. A further 860 mg (4.51 mmol) of p-toluenesulfonyl chloride are added, and the reaction solution is stirred at 60° C. for another hour. The suspension is filtered through Celite®, the celite is washed with THF and a little dichloromethane/methanol 10:1 and the solvent is removed under reduced pressure. The residue is reacted further as a crude product.

Yield: 1.65 g (86% of theory)

LC-MS (Method 1): $R_t$=239 min.

Example 19A

N-[3-Fluoro-4-({1-[(4-methylphenyl)sulfonyl]-1H-pyrrolo[2,3-b]pyridin-4-yl}oxy)phenyl]acetamide

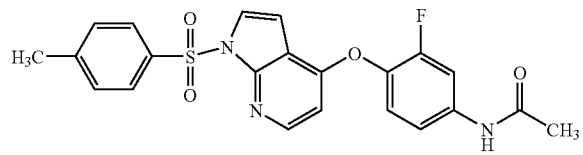

3.02 g (7.60 mmol) of 3-fluoro-4-({1-[(4-methylphenyl)sulfonyl]-1H-pyrrolo[2,3-b]pyridin-4-yl}oxy)aniline are dissolved in 30 ml of acetic anhydride and stirred at 50° C. for one hour. Volatile components are then removed under reduced pressure and excess reagent is repeatedly removed azeotropically using toluene. The crude product is purified on a silica gel column (mobile phase: cyclohexane/ethyl acetate 1:1).

Yield: 2.04 g (58% of theory)
LC-MS (Method 3): $R_t$=2.50 min.
MS (ESI pos.): m/z=440 (M+H)$^+$.
$^1$H-NMR (DMSO-$d_6$, 400 MHz): δ=2.07 (s, 3H), 2.35 (s, 3H), 6.55 (m, 1H), 6.66 (m, 1H), 7.34 (mc, 2H), 7.43 (d, 2H), 7.80 (m, 2H), 8.01 (d, 2H), 8.20 (d, 1H), 10.26 (s, 1H).

Example 20A

N-[4-({3-Bromo-1-[(4-methylphenyl)sulfonyl]-1H-pyrrolo[2,3-b]pyridin-4-yl}oxy)-3-fluorophenyl]acetamide

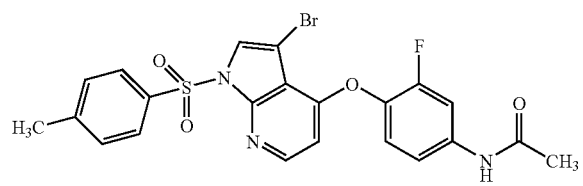

490 mg (1.11 mmol) of N-[3-fluoro-4-({1-[(4-methylphenyl)sulfonyl]-1H-pyrrolo[2,3-b]pyridin-4-yl}oxy)phenyl]acetamide are dissolved in 35 ml of dichloromethane and cooled to 0° C. 114 µl (2.23 mmol) of bromine are then added. After one hour, ice in 10% strength sodium thiosulfate solution are added. After extraction with dichloromethane, the organic phase is dried over magnesium sulfate and the solvent is removed under reduced pressure. The product is purified by chromatography on silica gel (mobile phase: dichloromethane:acetone:10:1).

Yield: 360 mg (62% of theory)
Alternative Preparation Method:
3.23 g (8.87 mmol) of N-{4-[(3-bromo-1H-pyrrolo[2,3-b]pyridin-4-yl)oxy]-3-fluorophenyl}acetamide are dissolved in 500 ml of THF and cooled to −78° C. 3.90 ml (9.76 mmol) of a 2.5M n-butyllithium solution are added, and the mixture is stirred for 15 min. 1.86 g (9.76 mmol) of p-toluenesulfonyl chloride are then added dropwise as a solution in 20 ml of THF. The reaction solution is allowed to warm to RT and stirred for one hour. Sodium bicarbonate solution is then added, and the mixture is extracted three times with ethyl acetate. The combined organic phases are dried over magnesium sulfate and the solvent is removed under reduced pressure.

Yield: 4.22 g (92% of theory)
LC-MS (Method 1): $R_t$ 2.53 min.
$^1$H-NMR (DMSO-$d_6$, 400 MHz): δ=2.07 (s, 3H), 2.36 (s, 3H), 6.50 (m, 1H), 7.34 (m, 2H), 7.44 (d, 2H), 7.80 (m, 1H), 8.02 (d, 2H), 8.08 (s, 1H), 8.23 (d, 1H), 10.23 (s, 1H).

Example 21A

N-[3-Fluoro-4-({3-methyl-1-[(4-methylphenyl)sulfonyl]-1H-pyrrolo[2,3-b]pyridin-4-yl}oxy)phenyl]acetamide

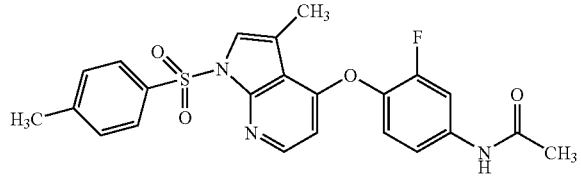

200 mg (0.39 mmol) of N-[4-({3-bromo-1-[(4-methylphenyl)sulfonyl]-1H-pyrrolo[2,3-b]pyridin-4-yl}oxy)-3-fluorophenyl]acetamide and 97 mg (1.16 mmol) of sodium bicarbonate are suspended in a mixture of dimethoxyethane (10 ml) and water (3 ml), and the mixture is degassed. 15.7 mg (0.02 mmol) of [1,1'-bis(diphenylphosphino)ferrocene]palladium(II) chloride/methylene dichloride complex and 107 µl (0.77 mmol) of trimethylboroxine are added, and the mixture is heated at 85° C. for two hours. For work-up, the reaction mixture is filtered through an Extrelut silica gel cartridge using 2 ml of dichloromethane/methanol 10:1, and the solvent is reduced under reduced pressure. The residue is purified by preparative HPLC.

Yield: 83 mg (47% of theory)
Alternative Preparation Method:
100 mg (0.19 mmol) of N-[4-({3-bromo-1-[(4-methylphenyl)sulfonyl]-1H-pyrrolo[2,3-b]pyridin-4-yl}oxy)-3-fluorophenyl]acetamide are dissolved in dioxane (2.5 ml). The solution is degassed and vented with argon. 0.29 ml (0.58 mmol) of a 2M solution of dimethylzinc in toluene and 7.9 mg (0.01 mmol) of [1,1'-bis(diphenylphosphino)ferrocene]palladium(II) chloride/methylene dichloride complex are added, and the mixture is heated at 100° C. for 2.5 hours. The mixture is allowed to cool to RT, acetic acid and 1M hydrochloric acid are added and the aqueous phase is extracted with ethyl acetate. The combined organic phases are dried over sodium sulfate and the solvent is removed under reduced pressure. The residue is purified by preparative HPLC.

Yield: 77 mg (86% of theory)
LC-MS (Method 3): $R_t$=2.60 min.
MS (ESI pos.): m/z=454 (M+H)$^+$.

¹H-NMR (DMSO-d₆, 400 MHz): δ 2.08 (s, 3H), 2.35 (s, 3H), 2.39 (s, 3H), 6.40 (d, 1H), 7.34 (m, 2H), 7.41 (d, 2H), 7.62 (m, 1H), 7.78 (m, 1H), 7.95 (d, 2H), 8.14 (d, 1H), 10.22 (s, 1H).

Example 22A

3-Methyl-1H-pyrrolo[2,3-b]pridine 7-oxide

Analogously to 1H-pyrrolo[2,3-b]pyridine 7-oxide, the title compound is obtained by oxidation of 11.0 g (54.1 mmol) of 3-methyl-1H-pyrrolo[2,3-b]pyridine (Hands, D.; Bishop, B.; Cameron, M.; Edwards, T. S.; Cottrell, I. F.; Wright, S. H. B.; Synthesis 1996 (7), 877-882) using 24.2 g (108 mmol) of 3-chloroperbenzoic acid.

Yield: 5.4 g (67% of theory)

LC-MS (Method 3): $R_t$=1.19 min.

MS (ESI pos.): m/z=149 (M+H)+

¹H-NMR (DMSO-d₆, 300 MHz): δ=2.25 (m, 3H), 7.05 (m, 1H), 7.21 (s, 1H), 7.59 (m, 1H), 8.10 (s, 1H), 12.06 (s, 1H).

Example 23A

4-Chloro-3-methyl-1H-pyrrolo[2,3-b]pyridine

1.00 g (6.75 mmol) of 3-methyl-1H-pyrrolo[2,3-b]pyridine 7-oxide is suspended in 5 ml of phosphoryl chloride. 2 ml of chloroform are then added, and the mixture is heated at reflux temperature overnight. The mixture is allowed to cool to RT and poured into ethyl acetate/ice-water. Solid sodium carbonate is then added. The phases are separated and the aqueous phase is washed with ethyl acetate. The organic phases are dried with sodium sulfate and concentrated. The residue is purified by column chromatography (silica gel 60, mobile phase: cyclohexane/methanol=4:1).

Yield: 200 mg (18% of theory)

LC-MS (Method 3): $R_t$=2.05 min.

¹H-NMR (DMSO-d₆, 200 MHz): δ=2.41 (m, 3H), 7.10 (d, 1H), 7.31 (s, 1H), 8.07 (d, 1H), 12.44 (s, 1H).

Example 24A

4-Chloro-3-methyl-1H-pyrrolo[2,3-b]pyridine 7-oxide

Analogously to 3-methyl-1H-pyrrolo[2,3-b]pyridine 7-oxide, the title compound is obtained by oxidation of 898 mg (5.39 mmol) of 4-chloro-3-methyl-1H-pyrrolo[2,3-b]pyridine (from Example 23A) using mit 2.42 g (10.78 mmol) of 3-chloroperbenzoic acid.

Yield: 688 mg (70% of theory)

LC-MS (Method 3): $R_t$=1.75 min.

MS (ESI pos.): m/z=183 (M+H)+

¹H-NMR (DMSO-d₆, 200 MHz): δ=2.41 (m, 3H), 7.10 (d, 1H), 7.30 (s, 1H), 8.07 (d, 1H), 12.44 (s, 1H).

Example 25A

Methyl 4,6-dichloro-3-methyl-1H-pyrrolo[2,3-b]pyridine-1-carboxylate

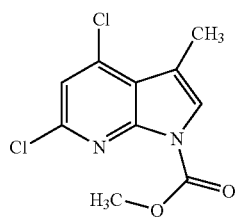

Analogously to 6-chloro-4-nitro-1H-pyrrolo[2,3-b]pyridine, the title compound is obtained from 688 mg (3.77 mmol) of 4-chloro-3-methyl-1H-pyrrolo[2,3-b]pyridine 7-oxide and 1.78 g (18.84 mmol) of methyl chloroformate and 0.61 g (3.77 mmol) of hexamethyldisilazane.

Yield: 215 mg (22% of theory)

LC-MS (Method 3): $R_t$=2.44 min.

MS (ESI pos.): m/z=259 (M+H)⁺.

¹H-NMR (DMSO-d₆, 200 MHz): δ=2.40 (m, 3H), 3.99 (s, 3H), 7.61 (s, 1H), 7.77 (d, 1H).

Example 26A

4-[(6-Chloro-3-methyl-1H-pyrrolo[2,3-b]pyridin-4-yl)oxy]-3-fluoroaniline

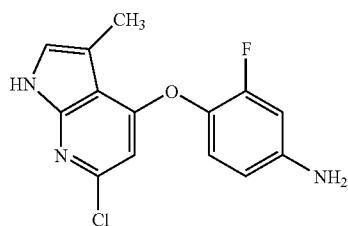

300 mg (1.16 mmol) of methyl-4,6-dichloro-3-methyl-1H-pyrrolo[2,3-b]pyridine-1-carboxylate and 320 mg (2.32 mmol) of powdered potassium carbonate are suspended in 9 ml of DMSO. The mixture is degassed, and 442 mg (3.48 mmol) of 4-amino-2-fluorophenol are added. The mixture is heated at 120° C. for 4 hours. After addition of ethyl acetate, the mixture is filtered off with suction through Celite®, and the celite is washed with ethyl acetate. The filtrate is shaken three times with saturated sodium bicarbonate solution and with saturated sodium chloride solution. The filtrate is dried over sodium sulfate and the solvent is removed under reduced pressure. The residue is purified by column chromatography (silica gel 60, mobile phase: dichloromethane/methanol=50:1).

Yield: 142 mg (42% of theory)
LC-MS (Method 3): $R_t$=2.32 min.
MS (ESI pos.): m/z 292 (M+H)$^+$.

Example 27A

3-Fluoro-4-[(3-methyl-1H-pyrrolo[2,3-b]pyridin-4-yl)oxy]aniline

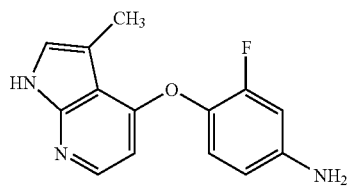

Analogously to 3-fluoro-4-(1H-pyrrol[2,3-b]pyridin-4-yloxy)aniline, the title compound is obtained by catalytic hydrogenation of 142 mg (0.49 mmol) of 4-[(6-chloro-3-methyl-1H-pyrrolo[2,3-b]pyridin-4-yl)oxy]-3-fluoroaniline.

Yield: 125 mg (100% of theory)

Alternative Preparation Method:

267 mg (0.59 mmol) of N-[3-fluoro-4-({3-methyl-1-[(4-methylphenyl)sulfonyl]-1H-pyrrolo[2,3-b]-pyridin-4-yl}oxy)phenyl]acetamide are dissolved in 10 ml of ethanol. 5 ml of 20% strength aqueous sodium hydroxide solution are added, and the reaction mixture is heated at 90° C. overnight. Most of the solvent is removed under reduced pressure. The residue is taken up in ethyl acetate and shaken with sodium carbonate solution. The organic phase is washed with sodium chloride solution and dried over magnesium sulfate, and the solvent is removed under reduced pressure.

Yield: 170 mg (97% of theory)
LC-MS (Method 3): $R_t$=1.52 min.
$^1$H-NMR (DMSO-d$_6$, 300 MHz): δ=2.41 (s, 3H), 5.38 (s, 2H), 6.08 (d, 1H), 6.40-6.56 (m, 2H), 7.00 (t, 1H), 7.08 (s, 1H), 7.93 (d, 1H), 11.26 (s, 1H).

Example 28A 2,2,2-Trifluoro-N-[3-fluoro-4-(1H-pyrrolo[2,3-b]pyridin-4-yloxy)phenyl]acetamide

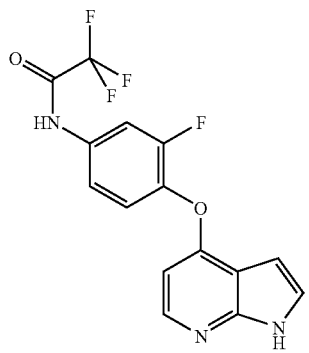

At 0° C., 0.5 ml of trifluoroacetic anhydride (3.48 mmol) is added dropwise to a solution of 650 mg (2.34 mmol) of 3-fluoro-4-(1H-pyrrolo[2,3-b]pyridin-4-yloxy)aniline and 0.65 ml (4.64 mmol) of triethylamine in anhydrous dichloromethane (40 ml). The mixture is stirred at 0° C. for 20 min, and the reaction is terminated by dropwise addition of a saturated sodium bicarbonate solution (20 ml). The suspension is allowed to warm to RT, and the phases are separated. The aqueous phase is extracted with ethyl acetate (20 ml). The combined organic phases are washed with a saturated sodium chloride solution. The organic solution is dried over magnesium sulfate and concentrated. This gives a solid which is not purified any further.

Yield: 830 mg (96% of theory)
HPLC (Method 3): $R_t$=2.15 min.
MS (ESI pos.): m/z=340 (M+H)$^+$.
$^1$H-NMR (DMSO-d$_6$, 400 MHz): δ=6.24 (m, 1H), 6.40 (d, 1H), 7.39 (dd, 1H), 7.46 (t, 1H), 7.59 (m, 1H), 7.82 (dd, 1H), 8.09 (d, 1H), 11.57 (s, 1H), 11.82 (br. s, 1H).

Example 29A

N-{4-[(3-Chloro-1H-pyrrolo[2,3-b]pyridin-4-yl)oxy]-3-fluorophenyl}-2,2,2-trifluoroacetamide

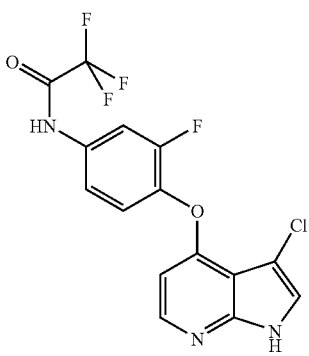

233 mg (1.75 mmol) of N-chlorosuccinimide are added to a solution of 540 mg (1.59 mmol) of 2,2,2-trifluoro-N-[3-fluoro-4-(1H-pyrrolo[2,3-b]pyridin-4-yloxy)phenyl]acetamide in anhydrous tetrahydrofuran (20 ml). The solution is stirred overnight. 20 ml of a saturated sodium bicarbonate solution are added, and the mixture is extracted with ethyl acetate (two times 20 ml). The combined organic phases are washed with a saturated sodium chloride solution. The organic phase is dried over magnesium sulfate and concentrated. This gives a solid which is not purified any further.

Yield: 639 mg (quantitative)
HPLC (Method 1): $R_t$=2.20 min.
MS (ESI pos.): m/z 374, 376 (M+H)$^+$.
$^1$H-NMR (DMSO-d$_6$, 300 MHz): δ=6.34 (d, 1H), 7.43 (t, 1H), 7.59 (m, 2H), 7.83 (dd, 1H), 8.12 (d, 1H), 11.54 (s, 1H), 12.12 (br. s, 1H).

Example 30A

4-[(3-Chloro-1H-pyrrolo[2,3-b]pyridin-4-yl)oxy]-3-fluoroaniline

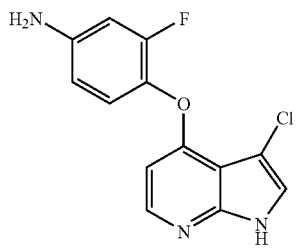

8 ml of 1N aqueous sodium hydroxide solution are added to a solution of 637 mg (1.70 mmol) of N-{4-[(3-chloro-1H-pyrrolo[2,3-b]pyridin-4-yl)oxy]-3-fluorophenyl}-2,2,2-trifluoroacetamide in tetrahydrofuran (10 ml). The reaction is stirred overnight. The solution is extracted with ethyl acetate (two times 20 ml). The combined organic phases are washed with a saturated sodium chloride solution. The organic phase is dried over magnesium sulfate and concentrated. This gives a solid which is not purified any further.

Yield: 396 mg (81% of theory)
HPLC (Method 1): $R_t$=1.78 min.
MS (ESI pos.): m/z=278, 280 (M+H)$^+$.

Example 31A

N-[4-({3-Cyclopropyl-1-[(4-methylphenyl)sulfonyl]-1H-pyrrolo[2,3-b]pyridin-4-yl}oxy)-3-fluorophenyl]acetamide

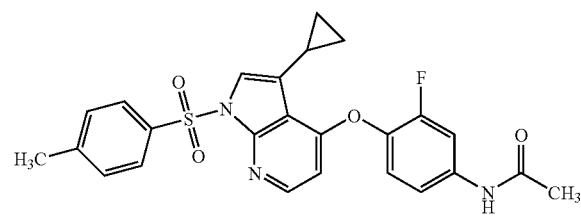

500 mg (0.96 mmol) of N-[4-({3-bromo-1-[(4-methylphenyl)sulfonyl]-1H-pyrrolo[2,3-b]pyridin-4-yl}oxy)-3-fluorophenyl]acetamide and 400 mg (2.89 mmol) of potassium carbonate are suspended in DMF (5 ml). The solution is degassed and vented with argon. 39 mg (0.05 mmol) of [1,1'-bis(diphenylphosphino)ferrocene]palladium(II) chloride/methylene dichloride complex and 207 mg (2.41 mmol) of cyclopropylboronic acid (Wallace, Debra J.; Chen, Cheng-yl; *Tetrahedron Lett.* 2002, 43(39), 6987-6990) are then added. The mixture is heated at 110° C. overnight. The reaction mixture is then dissolved in dichloromethane/methanol 10:1 and filtered through an Extrelut cartridge. The filtrate is concentrated under reduced pressure and the crude product is purified by preparative HPLC.

Yield: 194 mg (39% of theory)
LC-MS (Method 1): $R_t$=2.54 min.
MS (ESI pos.): m/z=480 (M+H)$^+$.
$^1$H-NMR (DMSO-d$_6$, 400 MHz): δ=0.73-0.78 (m, 2H), 0.85-0.91 (m, 2H), 2.07 (s, 3H), 2.15 (tt, 1H), 2.34 (s, 3H), 6.43 (d, 1H), 7.32-7.37 (m, 2H), 7.41 (d, 2H), 7.46 (s, 1H), 7.78-7.84 (m, 1H), 7.96 (d, 2H), 8.14 (d, 1H), 10.24 (br. s, 1H).

Example 32A

4-[(3-Cyclopropyl-1H-pyrrolo[2,3-b]pyidin-4-yl)oxy]-3-fluoroaniline

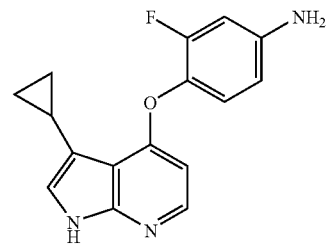

192 mg (0.40 mmol) of N-[4-({3-cyclopropyl-1-[(4-methylphenyl)sulfonyl]-1H-pyrrolo[2,3-b]-pyridin-4-yl}oxy)-3-fluorophenyl]acetamide are dissolved in 7 ml of ethanol. 3.5 ml of 20% strength aqueous sodium hydroxide solution are added, and the reaction mixture is stirred at 90° C. overnight. The reaction mixture is partitioned between ethyl acetate and water. The aqueous phase is extracted with ethyl acetate. The combined organic phases are dried over sodium sulfate, and the solvent is removed under reduced pressure. The crude product is reacted without further purification.

Yield: 99 mg (87% of theory)
LC-MS (Method 1): $R_t$=1.57 min.
MS (ESI pos.): m/z=0.284 (M+H)$^+$.
$^1$H-NMR (DMSO-d$_6$, 300 M 5) 0.57-0.64 (m, 2H), 0.77-0.85 (m, 2H), 2.12-2.23 (m, 1H), 5.37 (br. s, 2H), 6.11 (d, 1H), 6.44 (dd, 1H), 6.52 (dd, 1H), 6.95-7.05 (m, 2H), 7.94 (d, 1H), 11.28

Example 33A

N-[3-Fluoro-4-({1-[(4-methylphenyl)sulfonyl]-3-vinyl-1H-pyrrolo[2,3-b]pyridin-4-yl}oxy)phenyl]acetamide

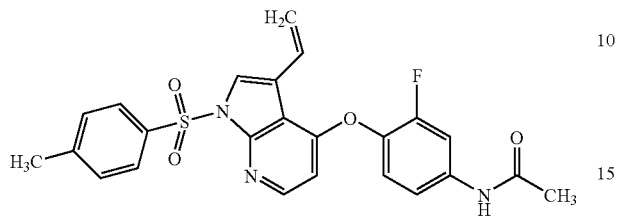

1.00 g (1.93 mmol) of N-[4-({3-bromo-1-[(4-methylphenyl)sulfonyl]-1H-pyrrolo[2,3-b]pyridin-4-yl}oxy)-3-fluorophenyl]acetamide and 800 mg (5.79 mmol) of potassium carbonate are suspended in DMF (6 ml). The solution is degassed and vented with argon. 79 mg (0.110 mmol) of [1,1'-bis(diphenylphosphino)ferrocene]palladium(II) chloride/methylene dichloride complex and 0.85 ml (3.86 mmol) of di-n-butyl vinylboronate are then added, and the mixture is stirred at 90° C. for 3 hours. After addition of sodium bicarbonate solution, the mixture is extracted three times with dichloromethane. The combined organic phases are concentrated, and the crude product is purified by chromatography on silica gel (mobile phase: dichloromethane/acetone 20:1 to 10:1).

Yield: 801 mg (89% of theory)
LC-MS (Method 3): $R_t$=2.69 min.
MS (ESI pos.): m/z=466 (M+H)$^+$.
$^1$H-NMR (DMSO-d$_6$, 400 MHz): δ 2.07 (s, 3H), 2.35 (s, 3H), 5.31 (d, 1H), 5.98 (d, 1H), 6.45 (d, 1H), 7.00 (dd, 1H), 7.33-7.40 (m, 2H), 7.44 (d, 2H), 7.79-7.85 (m, 1H), 8.02 (d, 2H), 8.14 (s, 1H), 8.18 (d, 1H), 10.27 (br. s, 1H).

Example 34A

N-[4-({3-Ethyl-1-[(4-methylphenyl)sulfonyl]-1H-pyrrolo[2,3-b]pyridin-4-yl}oxy)-3-fluorophenyl]acetamide

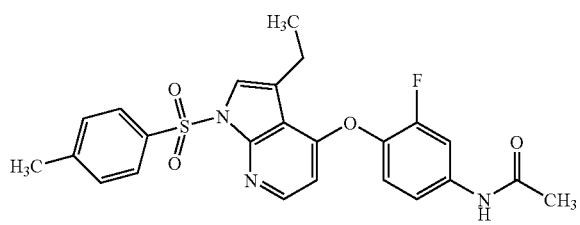

82 mg (0.18 mmol) of N-[3-fluoro-4-({1-[(4-methylphenyl)sulfonyl]-3-vinyl-1H-pyrrolo[2,3-b]-pyridin-4-yl}oxy)phenyl]acetamide are dissolved in 25 ml of ethanol. 19 mg (0.02 mmol) of 10% palladium-on-carbon are added, and the mixture is hydrogenated under a hydrogen atmosphere of 1.5 atm overnight. The mixture is then filtered through Celite® and the solvent is removed under reduced pressure. The product is reacted further without further purification.

Yield: 60 mg (73% of theory)
LC-MS (Method 1): $R_t$=2.54 min.
MS (ESI pos.): m/z=468 (M+H)$^+$.

$^1$H-NMR (DMSO-d$_6$, 300 MHz): δ=1.27 (t, 3H), 2.07 (s, 3H), 2.35 (s, 3H), 2.81 (dq, 2H), 6.40 (dd, 1H), 7.33-7.36 (m, 2H), 7.41 (d, 2H), 7.58 (s, 1H), 7.77-7.84 (m, 1H), 7.98 (d, 2H), 8.14 (d, 1H), 10.24 (br. s, 1H).

Example 35A

4-[(3-Ethyl-1H-pyrrolo[2,3-b]pyridin-4-yl)oxy]-3-fluoroaniline

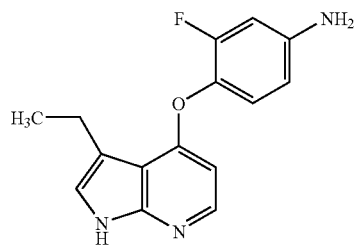

50 mg (0.11 mml) of N-[4-({3-ethyl-1-[(4-methylphenyl)sulfonyl]-1H-pyrrolo[2,3-b]pyridin-4-yl}oxy)-3-fluorophenyl]acetamide are dissolved in 3 ml of ethanol. 1 ml of 1N aqueous sodium hydroxide solution is added, and the mixture is stirred at 90° C. overnight. The reaction solution is partitioned between ethyl acetate and saturated sodium bicarbonate solution. The aqueous phase is extracted with ethyl acetate. The combined organic phases are dried over magnesium sulfate and concentrated. The crude product obtained is reacted without further purification.

Yield: 24.8 mg (85% of theory)
LC-MS (Method 1): $R_t$=1.53 min.
MS (ESI pos.): m/z=272 (M+H)$^+$.

Example 36A

N-[3-Fluoro-4-({3-(2-hydroxyethyl)-1-[(4-methylphenyl)sulfonyl]-1H-pyrrolo[2,3-b]pyridin-4-yl}oxy)phenyl]acetamide

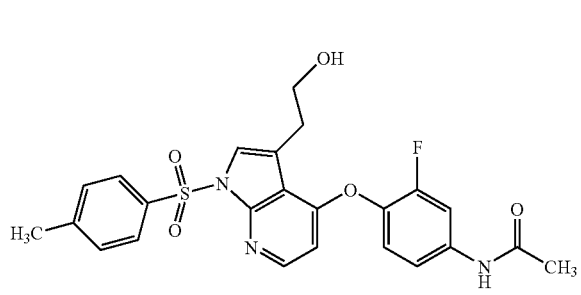

At 0° C., 890 mg (1.91 mmol) of N-[3-fluoro-4-({1-[(4-methylphenyl)sulfonyl]-3-vinyl-1H-pyrrolo[2,3-b]-pyridin-4-yl}oxy)phenyl]acetamide are initially charged in 28 ml of THF. 7.65 ml (7.65 mmol) of a 1M solution of borane in THF are added dropwise, and the mixture is stirred at RT for one hour. 14 ml of 1N aqueous sodium hydroxide solution and 14 ml of 30% strength hydrogen peroxide solution are then added carefully to the reaction mixture. The mixture is heated at 60° C. for one hour. For work-up, the reaction solution is partitioned between ethyl acetate and sodium bicarbonate solution. The aqueous phase is extracted with ethyl acetate and the combined organic phases are dried over sodium sulfate. The solvent is removed under reduced pressure. The product is purified by chromatography-on silica gel (mobile phase: dichloromethane/acetone 20:1 to 6.5:1).

Yield: 473 mg (51% of theory)
LC-MS (Method 1): $R_t$=2.00 min.
MS (ESI pos.): m/1484 (M+H)$^+$.
$^1$H-NMR (DMSO-$d_6$, 400 MHz): δ 2.07 (s, 3H), 2.35 (s, 3H), 2.95 (t, 2H), 3.72 (q, 2H), 4.69 (t, 1H), 6.39 (d, 1H), 7.32-7.39 (m, 2H), 7.42 (d, 2H), 7.63 (s, 1H), 7.79-7.83 (m, 1H), 7.98 (d, 2H), 8.14 (d, 1H), 10.26 (br. s, 1H).

Example 37A

2-[4-(4-Amino-2-fluorophenoxy)-1H-pyrrolo[2,3-b]pyridin-3-yl]ethanol

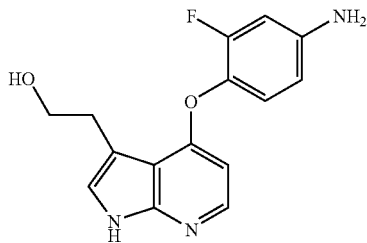

470 mg (0.97 mmol) of N-[3-fluoro-4-({3-(2-hydroxyethyl)-1-[(4-methylphenyl)sulfonyl]-1H-pyrrolo-[2,3-b]pyridin-4-yl}oxy)phenyl]acetamide are dissolved in 25 ml of ethanol. 10 ml of 20% strength aqueous sodium hydroxide solution are added, and the reaction mixture is stirred at 90° C. overnight. Most of the solvent is removed under reduced pressure, the residue is taken up in ethyl acetate and partitioned between ethyl acetate and 1N aqueous sodium hydroxide solution and extracted. The organic phase is washed with 1N aqueous sodium hydroxide solution and dried over magnesium sulfate, and the solvent is removed under reduced pressure.

Yield: 248 mg (89% of theory)
LC-MS (Method 6): $R_t$=1.13 min.
MS (ESI pos.): m/z=288 (M+H)$^+$.
$^1$H-NMR (DMSO-$d_6$, 400 MHz): o=2.95 (t, 2H), 3.69 (q, 2H), 4.55 (t, 1H), 5.43 (br. s, 2H), 6.08 (d, 1H), 6.44 (dd, 1H), 6.52 (dd, 1H), 7.01 (t, 1H), 7.13 (d, 1H), 7.94 (d, 1H), 11.37 (br. s, 1H).

Example 38A

2-{4-[4-(Acetylamino)-2-fluorophenoxy]-1-[(4-methylphenyl)sulfonyl]-1H-pyrrolo[2,3-b]pyridin-3-yl}ethyl 4-methylbenzenesulfonate

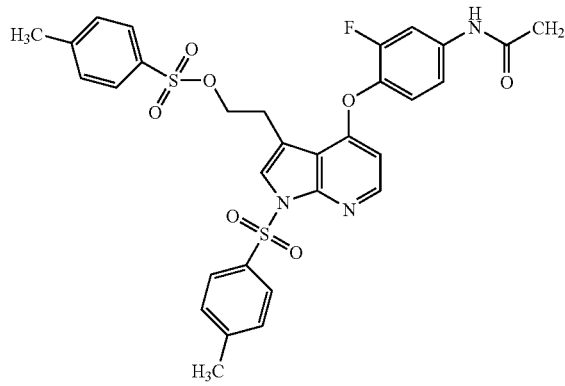

50 mg (0.10 mmol) of N-[3-fluoro-4-({3-(2-hydroxyethyl)-1-[(4-methylphenyl)sulfonyl]-1H-pyrrolo-[2,3-b]pyridin-4-yl}oxy)phenyl]acetamide are initially charged in 2.0 ml of dichloromethane. 25 μl (0.31 mmol) of pyridine and 19.7 mg (0.10 mmol) of p-toluenesulfonyl chloride are added, and the mixture is stirred at RT overnight. Two more times, the same amounts of pyridine and p-toluenesulfonyl chloride are added, at intervals of 2 hours. After the reaction has come to completion, the reaction solution is diluted with ethyl acetate and extracted twice with saturated ammonium chloride solution. The organic phase is dried over magnesium sulfate and the solvent is removed under reduced pressure. The crude product is purified by preparative HPLC.

Yield: 26 mg (38% of theory)
LC-MS (Method 3): $R_t$=2.68 min.
MS (ESI pos.): m/z=638 (M+H)$^+$.
$^1$H-NMR (DMSO-$d_6$, 300 MHz): δ=2.08 (s, 3H), 2.20 (s, 3H), 2.35 (s, 3H), 3.08 (t, 2H), 4.35 (t, 2H), 6.28 (dd, 1H), 6.97 (d, 2H), 7.22 (t, 1H), 7.33-7.39 (m, 1H), 7.40-7.47 (m, 4H), 7.65 (s, 1H), 7.79 (dd, 1H), 8.01 (d, 2H), 8.11 (d, 1H), 10.24 (br. s, 1H).

Example 39A

N-(3-Fluoro-4-{[3-(2-methoxyethyl)-1H-pyrrolo[2,3-b]pyridin-4-yl]oxy}phenyl)acetamide

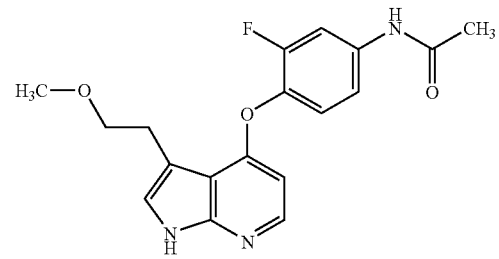

150 mg (0.24 mmol) of 2-{4-[4-(acetylamino)-2-fluorophenoxy]-1-[(4-methylphenyl)sulfonyl]-1H-pyrrolo[2,3-b]pyridin-3-yl}ethyl 4-methylbenzenesulfonate are dissolved in 6 ml of methanol. 0.17 ml (0.94 mmol) of a 5.4M sodium methoxide solution is added, and the mixture is stirred at 45° C. overnight. The reaction solution is partitioned between 1N aqueous sodium hydroxide solution and ethyl acetate. The aqueous phase is extracted with ethyl acetate and the combined organic phases are dried over magnesium sulfate. The solvent is removed under reduced pressure. The product obtained is reacted without further purification.

Yield: 55 mg (68% of theory)
LC-MS (Method 2): $R_t$=1.57 min.
MS (ESI pos.): m/z=344 (M+H)$^+$.
$^1$H-NMR (DMSO-$d_6$, 400 MHz): δ=2.08 (s, 3H), 3.02 (t, 2H), 3.23 (s, 3H), 3.62 (t, 2H), 6.15 (d, 1H), 7.20 (d, 1H), 7.30-7.38 (m, 2H), 7.79-7.84 (m, 1H), 7.99 (d, 1H), 10.24 (s, 1H), 11.49 (br. s, 1H).

Example 40A

3-Fluoro-4-{[3-(2-methoxyethyl)-1H-pyrrolo[2,3-b]pyridin-4-yl]oxy}aniline

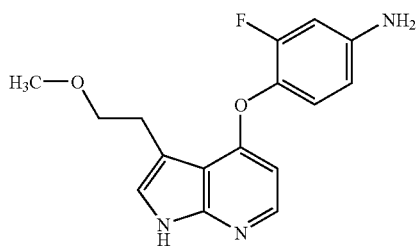

63 mg (0.18 mmol) of N-(3-fluoro-4-{[3-(2-methoxyethyl)-1H-pyrrolo[2,3-b]pyridin-4-yl]oxy}phenyl)acetamide are dissolved in 5 ml of ethanol. 2 ml of 20% strength aqueous sodium hydroxide solution are added, and the mixture is stirred at 90° C. overnight. The reaction mixture is then partitioned between ethyl acetate and 1N aqueous sodium hydroxide solution. The aqueous solution is extracted with ethyl acetate and the combined organic phases are washed with 1N aqueous sodium hydroxide solution. The organic phases are dried over magnesium sulfate and the solvent is removed under reduced pressure. The product is reacted further without purification.

Yield: 49 mg (89% of theory)
LC-MS (Method 1): $R_t$=1.27 min.
MS (ESI pos.): m/z=302 $(M+H)^+$.
$^1$H-NMR (DMSO-$d_6$, 300 MHz): δ=3.03 (t, 2H), 3.24 (s, 3H), 3.63 (t, 2H), 5.39 (br. s, 2H), 6.10 (d, 1H), 6.44 (dd, 1H), 6.53 (dd, 1H), 7.02 (t, 1H), 7.15 (d, 1H), 7.95 (d, 1H), 11.37 (br. s, 1H).

Example 41A

N-[4-{3-Cyano-1-[(4-methylphenyl)sulfonyl]-1H-pyrrolo[2,3-b]pyridin-4-yl}oxy)-3-fluorophenyl]acetamide (A) and N-{4-[(3-cyano-1H-pyrrolo[2,3-b]pyridin-4-yl)oxy]-3-fluorophenyl}acetamide (B)

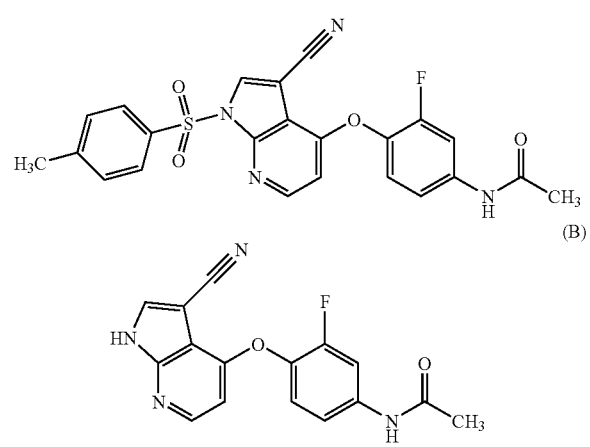

150 mg (0.29 mmol) of N-[4-({3-bromo-1-[(4-methylphenyl)sulfonyl]-1H-pyrrolo[2,3-b]pyridin-4-yl}oxy)-3-fluorophenyl]acetamide, 21.2 mg (0.12 mmol) of zinc acetate, 7.6 mg (0.12 mmol) of zinc dust, 18.4 mg (0.16 mmol) of zinc cyanide, 4.8 mg (0.087 mmol) of bis(diphenylphosphino)ferrocene and 2.65 mg (0.029 mmol) of tris(dibenzylideneacetone)dipalladium are initially charged in a test tube with a screw-on cap. Under argon, a degassed mixture of 1 ml of DMF and 0.01 ml of water is added, and a closed vessel is heated at 100° C. for 15 hours. The crude mixture is purified by preparative HPLC. This gives a mixture of the tosylated (A) and detosylated compound (B) which is reacted further without purification.

Yield: 101 mg (17% of theory A, 82% of theory B)
LC-MS (Method 1): $R_t$=1.47 min. (B); 2.29 min. (A)
MS (ESI pos.): m/z=311 $(M+H)^+$ (B), 465 $(M+H)^+$ (A).
$^1$H-NMR (DMSO-$d_6$, 300 MHz, compound A): δ=2.08 (s, 3H), 2.38 (s, 3H), 6.61 (d, 1H), 7.35-7.44 (m, 2H), 7.48 (d, 2H), 7.83 (dd, 1H), 8.08 (d, 2H), 8.31 (d, 1H), 8.95 (s, 1H), 10.29 (s, 1H).

Example 42A 4-(4-Amino-2-fluorophenoxy)-1H-pyrrolo[2,3-b]pyridine-3-carbonitrile

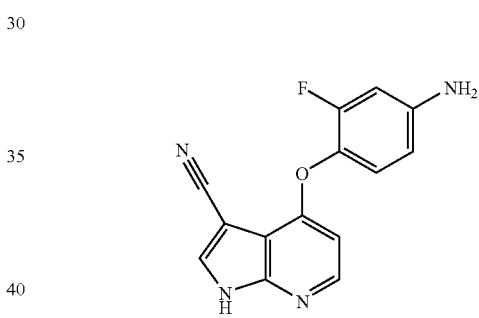

30 mg (0.065 mmol) of N-[4-({3-cyano-1-[(4-methylphenyl)sulfonyl]-1H-pyrrolo[2,3-b]pyridin-4-yl}oxy)-3-fluorophenyl]acetamide are dissolved in a mixture of 3 ml of ethanol and 3 ml of THF. 1.5 ml of 20% strength aqueous sodium hydroxide solution are added, and the mixture is heated at 90° C. overnight. Another 1 ml of 20% strength aqueous sodium hydroxide solution is then added, and a further ml after 6 hours. The mixture is again stirred overnight. The reaction mixture is then partitioned between ethyl acetate and water. The aqueous phase is extracted with ethyl acetate. The combined organic phases are dried over magnesium sulfate and the solvent is removed under reduced pressure. The crude product is reacted without further purification.

Yield: 19 mg (100% of theory)
LC-MS (Method 3): R=1.70 min.
MS (ESI pos.): m/z=269 $(M+H)^+$.
$^1$H-NMR (DMSO-$d_6$, 300 MHz): δ=5.48 (br. s, 2H), 6.30 (d, 1H), 6.45 (dd, 1H), 6.54 (dd, 1H), 7.07 (t, 1H); 8.14 (d, 1H), 8.31 (s, 1H), 12.7 (br. s, 1H).

Example 43A

N-[4-({3-Cyano-1-[(4-methylphenyl)sulfonyl]-1H-pyrrolo[2,3-b]pyridin-4-yl}oxy)-3,5-difluorophenyl]acetamide (A) and N-{4-[(3-cyano-1H-pyrrolo[2,3-b]pyridin-4-yl)oxy]-3,5-difluorophenyl}acetamide (B)

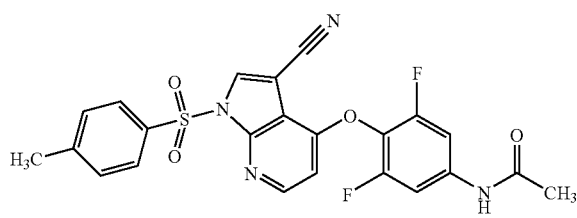

(A)

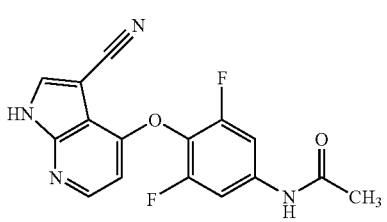

(B)

2.90 g (5.41 mmol) of N-[4-({3-bromo-1-[(4-methylphenyl)sulfonyl]-1H-pyrrolo[2,3-b]pyridin-4-yl}oxy)-3,5-difluorophenyl]acetamide, 397 mg (2.16 mmol) of zinc acetate, 141 mg (2.16 mmol) of zinc dust, 343 mg (2.92 mmol) of zinc cyanide, 89.9 mg (0.16 mmol) of bis(diphenylphosphino)ferrocene and 49.5 mg (0.05 mmol) of tris(dibenzylideneacetone)dipalladium are initially charged. Under argon, a degassed mixture of 33 ml of DMF and 0.33 ml of water is added, and the mixture is heated at 100° C. for 20 hours. The crude mixture is filtered through a short silica gel column (mobile phase: dichloromethane:methanol=3:1). The resulting product, 5 g of an oil comprising 37% of (A) and 31% of (B), is reacted further without further purification. An analytical amount is purified by preparative HPLC.

LC-MS (Method 3): $R_t$=1.86 min. (B); 2.61 min. (A)
MS (ESI pos.): m/z=329 (M+H)$^+$ (B), 483 (M+H)$^+$ (A).
$^1$H-NMR (DMSO-$d_6$, 400 MHz, compound A): δ=2.10 (s, 3H), 2.38 (s, 3H), 6.78 (d, 1H), 7.48 (d, 2H), 7.55 (d, 2H), 8.09 (d, 2H), 8.34 (d, 1H), 8.98 (s, 1H), 10.45 (s, 1H).
$^1$H-NMR (DMSO-$d_6$, 400 MHz, compound B): δ=2.11 (s, 3H), 6.54 (d, 1H); 7.57 (d, 2H), 8.23 (d, 1H), 8.45 (s, 1H), 10.45 (s, 1H), 12.99 (s, 1H).

Example 44A 4-(4-Amino-2,6-fluorophenoxy)-1H-pyrrolo[2,3-b]pyridine-3-carbonitrile

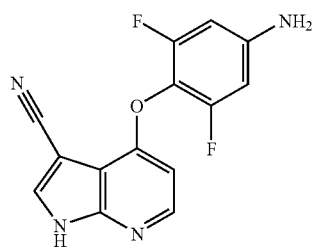

4.8 g of the crude product of the conversion into N-[4-({3-cyano-1-[(4-methylphenyl)sulfonyl]-1H-pyrrolo[2,3-b]pyridin-4-yl}oxy)-3,5-difluorophenyl]acetamide and N-{4-[(3-cyano-1H-pyrrolo[2,3-b]pyridin-4-yl)oxy]-3,5-difluorophenyl}acetamide are suspended in 40 ml of THF and 150 ml of ethanol. 50 ml of 20% strength aqueous sodium hydroxide solution are added, and the mixture is stirred at 90° C. for 20 h. After cooling, the mixture is concentrated under reduced pressure and water and ethyl acetate are added. The organic phase is separated off and clarified over activated carbon. The organic phase is dried over sodium sulfate and concentrated, giving a crystalline residue which is reacted without further purification. An analytical sample is purified by HPLC.

Yield: 1.60 g (61% of theory)
LC-MS (Method 3): $R_t$=1.89 min.
MS (ESI pos.): m/z=287 (M+H)$^+$.
$^1$H-NMR (DMSO-$d_6$, 400 MHz): δ=5.84 (s, 2H), 6.41 (d, 2H), 6.47 (d, 1H), 8.22 (d, 1H), 8.41 (s, 1H), 12.92 (s, 1H).

Example 45A

N-[4-({3-Cyclopropyl-1-[(4-methylphenyl)sulfonyl]-1H-pyrrolo[2,3-b]pyridin-4-yl}oxy)-3,5-difluorophenyl]acetamide

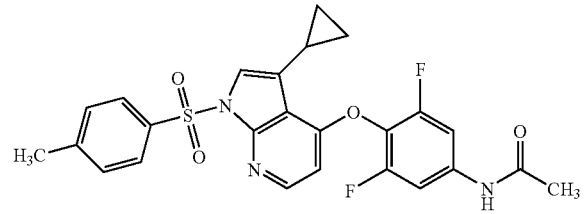

1.00 g (1.86 mmol) of N-[4-({3-bromo-1-[(4-methylphenyl)sulfonyl]-1H-pyrrolo[2,3-b]pyridin-4-yl}oxy)-3,5-difluorophenyl]acetamide, 1.12 g (13.1 mmol) of cyclopropylboronic acid (Wallace, Debra J.; Chen, Cheng-yi; *Tetrahedron Lett.* 2002, 43(39), 6987-6990), 52.3 mg (0.19 mmol) of tricyclohexylphosphine and 1.39 g (6.53 mmol) of potassium phosphate are suspended in 10 ml of toluene and 0.5 ml of water. The solution is degassed, and 20.9 mg (0.09 mmol) of palladium(II) acetate are added. The mixture is heated at 100° C. for 1.5 h. After cooling, ethyl acetate is added and the organic phase is separated off and washed twice with water. The organic phase is dried over sodium sulfate and concentrated. The product is purified by preparative HPLC.

Yield: 666 mg (72% of theory)
LC-MS (Method 1): $R_t$=2.59 min.
MS (ESI pos.): m/z=498 (M+H)$^+$.
$^1$H-NMR (DMSO-$d_6$, 300 MHz): δ=0.73-0.80 (m, 21H), 0.86-0.94 (m, 2H), 2.09 (s, 3H), 2.10-2.21 (m, 1H), 2.35 (s, 3H), 6.55 (d, 1H), 7.41 (d, 2H), 7.51 (s, 1H), 7.53 (d, 2H), 7.97 (d, 2H), 8.17 (d, 1H), 10.43 (s, 1H).

Example 46A

4-[(3-Cyclopropyl-1H-pyrrolo[2,3-b]pyridin-4-yl)oxy]-3,5-difluoroaniline

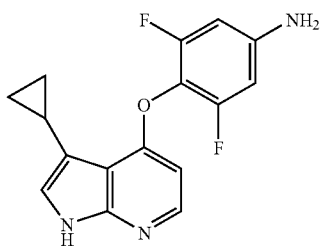

624 mg (1.25 mmol) of N-[4-({3-cyclopropyl-1-[(4-methylphenyl)sulfonyl]-1H-pyrrolo[2,3-b]-pyridin-4-yl}oxy)-3,5-difluorophenyl]acetamide are dissolved in 17 ml of ethanol. 10 ml of semiconcentrated aqueous sodium hydroxide solution are added, and the reaction mixture is stirred at 90° C. for 15 h. The reaction mixture is partitioned between ethyl acetate and water. The organic phase is washed twice with water, dried over sodium sulfate and concentrated under reduced pressure. This gives a crystalline residue.

Yield: 360 mg (92% of theory)
LC-MS (Method 1): $R_t$=1.73 min.
MS (ESI pos.): m/z=302 (M+H)$^+$.
$^1$H-NMR (DMSO-d$_6$, 300 MHz): δ=0.59-0.65 (m, 2H), 0.79-0.87 (m, 2H), 2.12-2.22 (m, 1H), 5.76 (br. s, 2H), 6.18 (d, 1H), 6.34-6.43 (m, 2H), 7.03 (d, 1H), 7.98 (d, 1H), 11.39 (s, 1H).

Example 47A

N-{4-[(3-Bromo-1-{[2-(trimethylsilyl)ethoxy]methyl}-1H-pyrrolo[2,3-b]pyridin-4-yl)oxy]-3,5-difluorophenyl}-2,2,2-trifluoroacetamide

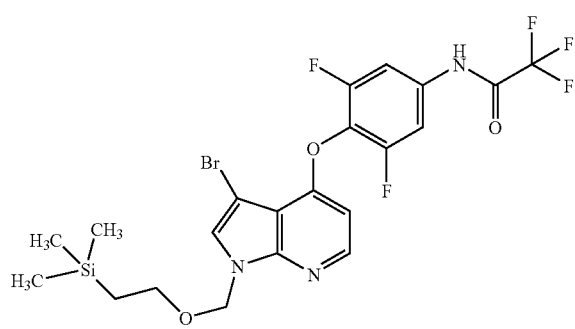

At 0° C., 485 µl of a 1M solution of bromine (490 µmol) in dichloromethane are added dropwise to a solution of 215 mg of N-{3,5-difluoro-4-[(1-{[2-trimethylsilyl)ethoxy]methyl}-1H-pyrrolo[2,3-b]pyridin-4-yl)oxy]phenyl}-2,2,2-trifluoroacetamide (440 µmol) in 10 ml of dichloromethane. After 15 min of stirring at 0° C., the reaction mixture is poured into a mixture of 10% strength sodium thiosulfate solution and ice, the mixture is extracted twice with ethyl acetate and the combined organic phases are dried over magnesium sulfate. After concentration under reduced pressure, the residue is purified by preparative HPLC.

Yield: 246 mg (98% of theory)
LC-MS (Method 1): R=3.05 min.
MS (ESI pos.): m/z=568 (M+H)$^+$.
$^1$H-NMR (DMSO-d$_6$, 400 MHz): δ=−0.01 (s, 9H), 0.82 (t, 2H), 3.53 (t, 2H), 5.60 (s, 2H), 6.48 (d, 1H), 7.70 (d, 2H), 7.88 (s, 1H), 8.17 (d, 1H), 11.72 (s, 1H).

Example 48A

4-[(3-Bromo-1H-pyrrolo[2,3-b]pyridin-4-yl)oxy]-3,5-difluoroaniline

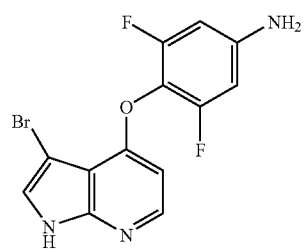

A solution of 201 mg of N-{4-[(3-bromo-1-{[2-(trimethylsilyl)ethoxy]methyl}-1H-pyrrolo[2,3-b]pyridin-4-yl)oxy]-3,5-difluorophenyl}-2,2,2-trifluoroacetamide (280 µmol) in 4.00 ml of a mixture of hydrogen chloride in dioxane (4N) is stirred at RT overnight, and the precipitated crystals are filtered off and washed with diethyl ether. The solid residue (131 mg) is dissolved in 20 ml of THF. 2.7 ml of a 5% strength solution of lithium hydroxide in water (5.62 mmol) are then added, and the mixture is stirred at RT for 60 h. The reaction mixture is diluted with water and extracted twice with ethyl acetate. After drying over magnesium sulfate, the combined organic phases are concentrated and the residue is purified by preparative HPLC.

Yield: 51 mg (51% of theory)
LC-MS (Method 3): $R_t$=2.50 min.
MS (ESI neg.): m/z=338 (M−H)$^-$.
$^1$H-NMR (DMSO-d$_6$, 400 MHz): δ=5.79 (s, 2H), 6.28 (d, 1H), 6.39 (d, 2H), 7.58-7.63 (m, 1H), 8.08 (d, 1H), 12.12 (s, 1H).

Working Examples

Example 1

6-Chloro-N$^4$-{3,5-difluoro-4-[(3-methyl-1H-pyrrolo[2,3-b]pyridin-4-yl)oxy]phenyl}pyrimidine-2,4-diamine

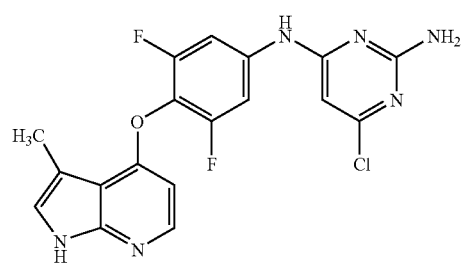

415 mg (1.51 mmol) of 3,5-difluoro-4-[(3-methyl-1H-pyrrolo[2,3-b]pyridin-4-yl)oxy]aniline and 321 mg (1.96 mmol)

of 4,6-dichloropyrimidine-2-amine are suspended in 8 ml of water. 1.96 ml of 1N hydrochloric acid are added, and the mixture is heated at reflux overnight. Using 1N aqueous sodium hydroxide solution, the pH is then adjusted to 10, resulting in the precipitation of crystals. The crystals are filtered off with suction and washed with water. The crude product is purified by column chromatography on silica gel (mobile phase: dichloromethane/methanol (7N ammonia) 100:1 to 100:5).

Yield: 575 mg (95% of theory)
LC-MS (Method 2): $R_t$=2.14 min.
MS (ESI pos.): m/z=403 (M+H)$^+$.
$^1$H-NMR (DMSO-d$_6$, 300 MHz): δ=2.44 (s, 3H), 6.04 (s, 1H), 6.20 (d, 1H), 7.00 (br. s, 21H), 7.16 (s, 1H), 7.70-7.78 (m, 2H), 7.99 (d, 1H), 9.78 (s, 1H), 11.44 (br. s, 1H).

Example 2

N$^4$-{3,5-Difluoro-4-[(3-methyl-1H-pyrrolo[2,3-b]pyridin-4-yl)oxy]phenyl}pyrimidine-2,4-diamine

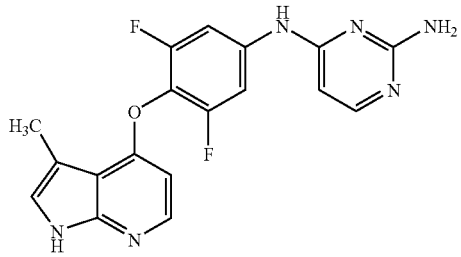

50 mg (0.12 mmol) of 6-chloro-N$^4$-{3,5-difluoro-4-[(3-methyl-1H-pyrrolo[2,3-b]pyridin-4-yl)oxy]phenyl}pyrimidine-2,4-diamine are dissolved in 10 ml of ethanol. 35 μl (0.25 mmol) of triethylamine and 26 mg (0.02 mmol) of 10% palladium-on-carbon are added, and the mixture is hydrogenated under atmospheric pressure in a hydrogen atmosphere overnight. The mixture is then filtered through Celite®, and the celite is washed with methanol. The solvent is removed under reduced pressure and the crude product is purified by preparative HPLC.

Yield: 31 mg (68% of theory)
LC-MS (Method 3): $R_t$=1.42 min.
MS (ESI pos.): m/z=369 (M+H)$^+$.
$^1$H-NMR (DMSO-d$_6$, 300 MHz): δ=2.44 (s, 3H), 6.02 (d, 1H), 6.20 (d, 1H), 6.42 (br. s, 2H), 7.15 (s, 1H), 7.73-7.80 (m, 2H), 7.89 (d, 1H), 7.99 (d, 1H), 9.53 (s, 1H), 11.39 (br. s, 1H).

Example 3

N$^4$-{3,5-Difluoro-4-[(3-methyl-1H-pyrrolo[2,3-b]pyridin-4-yl)oxy]phenyl}-6-(trifluoromethyl)pyrimidine-2,4-diamine

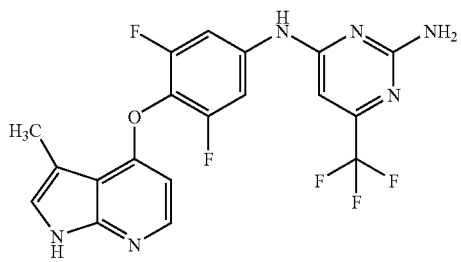

160 mg (0.58 mmol) of 3,5-difluoro-4-[(3-methyl-H-pyrrolo[2,3-b]pyridin-4-yl)oxy]aniline and 138 mg (0.70 mmol) of 4-chloro-6-(trifluoromethyl)pyrimidine-2-amine are suspended in 3.5 ml of water. 0.76 ml (0.76 mmol) of 1N hydrochloric acid is added, and the mixture is heated at reflux overnight. By addition of 1N aqueous sodium hydroxide solution, the pH is adjusted to 10, resulting in the precipitation of crystals. The crystals are filtered off with suction and purified by chromatography on silica gel (mobile phase: dichloromethane/methanol (7N ammonia) 100:1 to 100:3). The product obtained is purified further by preparative HPLC.

Yield: 112 mg (44% of theory)
LC-MS (Method 1): $R_t$=2.16 min.
MS (ESI pos.): m/z=437 (M+H)$^+$.
$^1$H-NMR (DMSO-d$_6$, 400 MHz): δ=2.44 (s, 3H), 6.22 (d, 1H), 6.37 (s, 1H), 7.11 (br. s, 2H), 7.17 (s, 1H), 7.75-7.82 (m, 2H), 8.00 (d, 1H)10.03 (s, 1H), 11.44 (br. s, 1H).

Example 4

N$^4$-{4-[(3-Chloro-1H-pyrrolo[2,3-b]pyridin-4-yl)oxy]-3,5-difluorophenyl}-6-(trifluoromethyl)pyrimidine-2,4-diamine

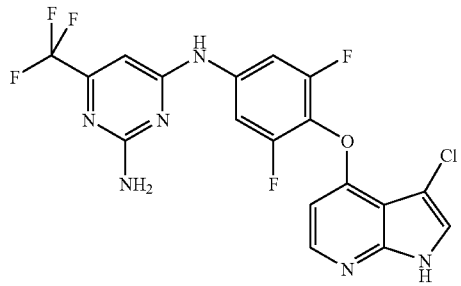

65 mg (0.22 mmol) of 3,5-difluoro-4-[(3-chloro-1H-pyrrolo[2,3-b]pyridin-4-yl)oxy]aniline and 47 mg (0.24 mmol) of 4-chloro-6-trifluoromethyl)pyrimidine-2-amine are suspended in 4 ml of water/ethanol 1:1. 25 μl (0.29 mmol) of 37% strength hydrochloric acid are added, and the mixture is heated at reflux overnight. Using 1N aqueous sodium hydroxide solution, the pH is adjusted to 7, and the mixture is extracted with ethyl acetate. The organic phase is washed with saturated sodium chloride solution, dried over magnesium sulfate and concentrated. The residue is purified by preparative HPLC.

Yield: 40 mg (39% of theory)
HPLC (Method 1): $R_t$=2.22 min.
MS (ESI pos.): m/z=439, 441 (M+H)$^+$.
$^1$H-NMR (DMSO-d$_6$, 300 MHz): o=6.28 (d, 1H), 6.38 (s, 1H), 6.99 (br. s, 2H), 7.33 (t, 1H), 7.40 (dd, 1H), 7.58 (s, 1H), 8.10 (d, 1H), 8.25 (dd, 1H), 9.91 (s, 1H), 12.05 (br. s, 1H).

Example 5

6-Chloro-$N^4$-{3-fluoro-4-[(3-methyl-1H-pyrrolo[2,3-b]pyridin-4-yl)oxy]phenyl}pyrimidine-2,4-diamine

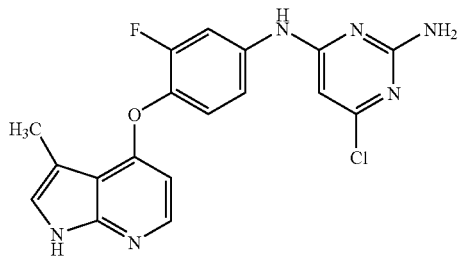

35 mg (0.14 mmol) of 3-fluoro-4-[(3-methyl-1H-pyrrolo[2,3-b]pyridin-4-yl)oxy]aniline and 24.5 mg (0.15 mmol) of 4,6-dichloropyrimidine-2-amine are suspended in 2.5 ml of water. 17 μl (0.18 mmol) of 37% strength hydrochloric acid are added, and the mixture is heated at reflux overnight. Using 1N aqueous sodium hydroxide solution, the pH is adjusted to 10, resulting in the precipitation of crystals. The crystals are filtered off with suction and purified by column chromatography on silica gel (mobile phase: dichloromethane:methanol (7N ammonia) 100:5).

Yield: 37 mg (67% of theory)
LC-MS (Method 1): $R_t$=1.73 min.
MS (ESI pos.): m/z=385 (M+H)$^+$.
$^1$H-NMR (DMSO-$d_6$, 300 MHz): δ=2.40 (d, 3H), 6.03 (s, 1H), 6.17 (dd, 1H), 6.84 (br. s, 2H), 7.12 (m, 1H), 7.23-7.36 (m, 2H), 7.98 (d, 1H), 8.14 (dd, 1H), 9.57 (s, 1H), 11.34 (br. s, 1H).

Example 6

$N^4$-{3-Fluoro-4-[(3-methyl-1H-pyrrolo[2,3-b]pyridin-4-yl)oxy]phenyl}pyrimidine-2,4-diamine

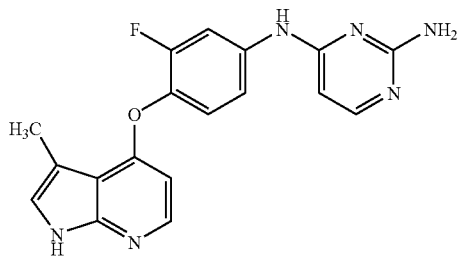

50 mg (0.13 mmol) of 6-chloro-$N^4$-{3-fluoro-4-[(3-methyl-1H-pyrrolo[2,3-b]pyridin-4-yl)oxy]phenyl}pyrimidine-2,4-diamine are dissolved in 10 ml of ethanol. 36 μl (0.26 mmol) of triethylamine and 28 mg (0.03 mmol) of 10% palladium-on-carbon are added, and the mixture is hydrogenated under atmospheric pressure in a hydrogen atmosphere overnight. The mixture is then filtered through Celite®, and the celite is washed with methanol. The solvent is removed under reduced pressure and the crude product is purified by preparative HPLC.

Yield: 24 mg (53% of theory)
LC-MS (Method 6): $R_t$=1.48 min.
MS (ESI pos.): m/z=351 (M+H)$^+$.
$^1$H-NMR (DMSO-$d_6$, 300 MHz): δ=2.41 (d, 3H), 6.02 (d, 1H), 6.16 (dd, 1H), 6.30 (br. s, 2H), 7.12 (s, 1H), 7.21-7.40 (m, 2H), 7.85 (d, 1H), 7.97 (d, 1H), 8.18 (dd, 1H), 9.36 (s, 1H), 11.33 (br. s, 1H).

Example 7

$N^4$-{3-Fluoro-4-[(3-methyl-1H-pyrrolo[2,3-b]pyridin-4-yl)oxy]phenyl}-6-(trifluoromethyl)pyrimidine-2,4-diamine

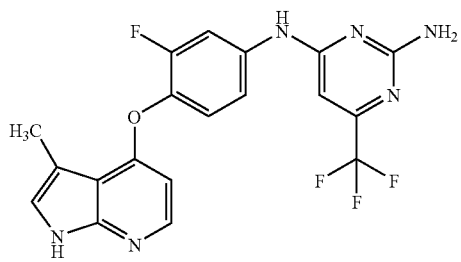

184 mg (0.72 mmol) of 3-fluoro-4-[(3-methyl-1H-pyrrolo[2,3-b]pyridin-4-yl)oxy]aniline and 170 mg (0.86 mmol) of 4-chloro-6-trifluoromethyl)pyrimidine-2-amine are suspended in 3.5 ml of water. 0.93 ml (0.93 mmol) of 1N hydrochloric acid is added, and the mixture is heated at reflux overnight. Using 1N aqueous sodium hydroxide solution, the suspension is adjusted to pH 10, resulting, in the precipitation of crystals. The crystals are filtered off with suction, washed with water and purified by column chromatography on silica gel (mobile phase: dichloromethane/methanol (7N ammonia) 100:1 to 100:3).

Yield: 212 mg (71% of theory)
LC-MS (Method 1): $R_t$=1.97 min.
MS (ESI pos.): m/z=419 (M+H)$^+$.
$^1$H-NMR (DMSO-$d_6$, 400 MHz): δ=2.41 (s, 3H), 6.17 (d, 1H), 6.38 (s, 1H), 7.00 (br. s, 2H), 7.14 (s, 1H), 7.30 (t, 1H), 7.38 (dd, 1H), 7.98 (d, 1H), 8.23 (dd, 1H), 9.87 (s, 1H), 11.38 (br. s, 1H).

Example 8

6-Chloro-$N^4$-{4-[(3-chloro-1H-pyrrolo[2,3-b]pyridin-4-yl)oxy]-3-fluorophenyl}pyrimidine-2,4-diamine

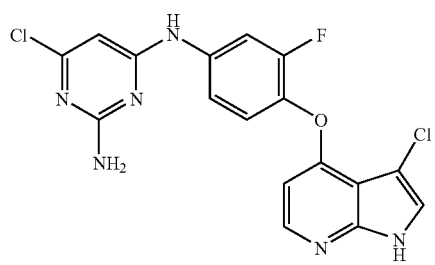

67 mg (0.24 mmol) of 3-fluoro-4-[(3-chloro-1H-pyrrolo[2,3-b]pyridin-4-yl)oxy]aniline and 40 mg (0.24 mmol) of 4,6-dichloropyrimidine-2-amine are suspended in 4 ml of water/ethanol 1:1. 25 μl (0.29 mmol) of 37% strength hydrochloric acid are added, and the mixture is heated at reflux overnight. Using 1N aqueous sodium hydroxide solution, the pH is adjusted to 7 and the mixture is extracted with ethyl acetate. The organic phase is washed with saturated sodium chloride solution, dried with magnesium sulfate and concentrated. The residue is purified by preparative HPLC.

Yield: 54 mg (53% of theory)

HPLC (Method 1): $R_t$=2.07 min.

MS (ESI pos.): m/z=405, 407 (M+H)$^+$.

$^1$H-NMR (DMSO-d$_6$, 300 MHz): o=6.05 (s, 1H), 6.27 (dd, 1H), 6.84 (br. s, 2H), 7.29 (t, 1H), 7.36 (m, 1H), 7.56 (s, 1H), 8.09 (d, 1H), 8.16 (dd, 1H), 9.62 (s, 1H), 12.03 (br. s, 1H).

Example 9

N$^4$-{4-[(3-Chloro-1H-pyrrolo[2,3-b]pyridin-4-yl)oxy]-3-fluorophenyl}-6-(trifluoromethyl)pyrimidine-2,4-diamine

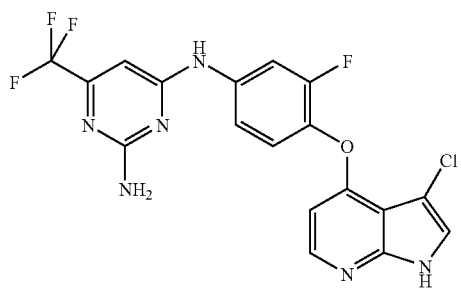

67 mg (0.24 mmol) of 3-fluoro-4-[(3-chloro-1H-pyrrolo[2,3-b]pyridin-4-yl)oxy]aniline and 47 mg (0.24 mmol) of 4-chloro-6-(trifluoromethyl)pyrimidine-2-amine are suspended in 4 ml of water/ethanol 1:1. 25 μl (0.29 mmol) of 37% strength hydrochloric acid are added, and the mixture is heated at reflux overnight. Using 1N aqueous sodium hydroxide solution, the pH is adjusted to 7, and the mixture is extracted with ethyl acetate. The organic phase is washed with saturated sodium chloride solution, dried with magnesium sulfate and concentrated. The residue is purified by preparative HPLC.

Yield: 40 mg (36% of theory)

HPLC (Method 1): $R_t$=2.22 min.

MS (ESI pos.): m/z=439, 441 (M+H)$^+$.

$^1$H-NMR (DMSO-d$_6$, 300 MHz): δ=6.28 (d, 1H), 6.38 (s, 1H), 6.99 (br. s, 2H), 7.33 (t, 1H), 7.40 (dd, 1H), 7.58 (s, 1H), 8.10 (d, 1H), 8.25 (dd, 1H), 9.91 (s, 1H), 12.05 (br. s, 1H).

Example 10

N$^4$-{4-[(3-Chloro-1H-pyrrolo[2,3-b]pyridin-4-yl)oxy]-3-fluorophenyl}pyrimidine-2,4-diamine

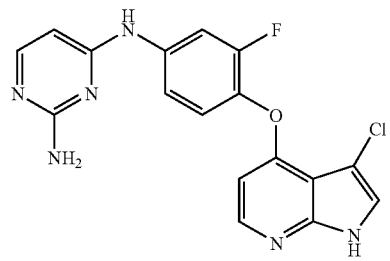

100 mg (0.36 mmol) of 4-[(3-chloro-0H-pyrrolo[2,3-b]pyridin-4-yl)oxy]-3-fluoroaniline and 60 mg (0.46 mmol) of 4-chloropyrimidine-2-amine are suspended in 4 ml of water/ethanol 1:1. 36 μl (0.43 mmol) of 37% strength hydrochloric acid are added, and the mixture is heated at reflux overnight. Using 1N aqueous sodium hydroxide solution, the pH is adjusted to 7, and the mixture is extracted with ethyl acetate. The organic phase is washed with saturated sodium chloride solution, dried over magnesium sulfate and concentrated. The residue is purified by preparative HPLC.

Yield: 68 mg (51% of theory)

HPLC (Method 1): $R_t$=1.42 min.

MS (ESI pos.): m/z=371, 373 (M+H)$^+$.

$^1$H-NMR (DMSO-d$_6$, 300 MHz): δ=6.05 (d, 1H), 6.26 (dd, 1H), 6.83 (br. s, 2H), 7.28 (t, 1H), 7.37 (m, 1H), 7.56 (s, 1H), 7.89 (d, 1H), 8.09 (d, 1H), 8.15 (dd, 1H), 9.12 (s, 1H), 12.07 (br. s, 1H).

Example 11

N$^4$-{4-[(3-Cyclopropyl-1H-pyrrolo[2,3-b]pyridin-4-yl)oxy]-3-fluorophenyl}-6-(trifluoromethyl)pyrimidine-2,4-diamine

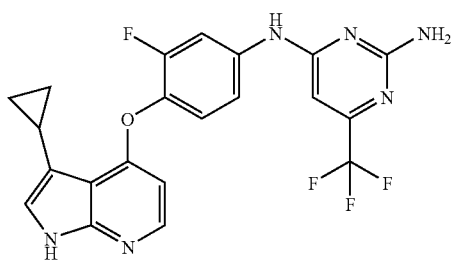

114 mg (0.40 mmol) of 4-[(3-cyclopropyl-1H-pyrrolo[2,3-b]pyridin-4-yl)oxy]-3-fluoroaniline and 95 mg (0.48 mmol) of 4-chloro-6-(trifluoromethyl)pyrimidine-2-amine are suspended in 3.5 ml of water. 0.52 ml (0.52 mmol) of 1N hydrochloric acid are added, and the mixture is heated at reflux overnight. Another 30 mg (0.15 mmol) of 4-chloro-6-(trifluoromethyl)pyrimidine-2-amine are then added, and the mixture is heated for another 6 hours. By addition of 1N aqueous sodium hydroxide solution, the pH is adjusted to 10, resulting in the precipitation of crystals. The crystals are filtered off with suction and purified by chromatography on silica gel (mobile phase: dichloromethane/methanol (7N ammonia) 100:1 to 100:3).

Yield: 94 mg (53% of theory)
LC-MS (Method 6): $R_t$=2.31 min.
MS (ESI pos.): m/z=445 (M+H)$^+$.
$^1$H-NMR (DMSO-d$_6$, 300 MHz): δ=0.59-0.65 (m, 2H), 0.77-0.85 (m, 2H), 2.10-2.20 (m, 1H), 6.21 (dd, 1H), 6.38 (s, 1H), 6.95 (br. s, 2H), 7.04 (d, 1H), 7.25-7.41 (m, 2H), 7.99 (d, 1H), 8.21 (dd, 1H), 9.83 (s, 1H), 11.38 (br. s, 1H).

Example 12

6-Chloro-N$^4$-{4-[(3-ethyl-1H-pyrrolo[2,3-b]pyridin-4-yl)oxy]-3-fluorophenyl}pyrimidine-2,4-diamine

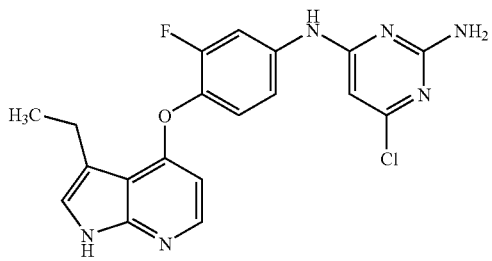

50 mg (0.18 mmol) of 4-[(3-ethyl-1H-pyrrolo[2,3-b]pyridin-4-yl)oxy]-3-fluoroaniline and 32 mg (0.19 mmol) of 4,6-dichloropyrimidine-2-amine are suspended in 5 ml of water. 27 μl of 37% strength hydrochloric acid are added, and the mixture is heated at reflux overnight. Using 1N aqueous sodium hydroxide solution, the pH is then adjusted to 10, resulting in the precipitation of crystals. The crystals are filtered off with suction and purified by preparative HPLC.

Yield: 26 mg (33% of theory)
LC-MS (Method 1): $R_t$=1.93 min.
MS (ESI pos.): m/z=399 (M+H)$^+$.
$^1$H-NMR (DMSO-d$_6$, 300 MHz): δ=1.27 (t, 3H), 2.83 (q, 2H), 6.04 (s, 1H), 6.16 (d, 1H), 6.83 (br. s, 2H), 7.14 (m, 1H), 7.24-7.37 (m, 2H), 7.98 (d, IF), 8.14 (dd, 1H), 9.57 (s, 1H), 11.36 (br. s, 1H).

Example 13

N$^4$-{4-[(3-Ethyl-1H-pyrrolo[2,3-b]pyridin-4-yl)oxy]-3-fluorophenyl}-6-(trifluoromethyl)pyrimidine-2,4-diamine

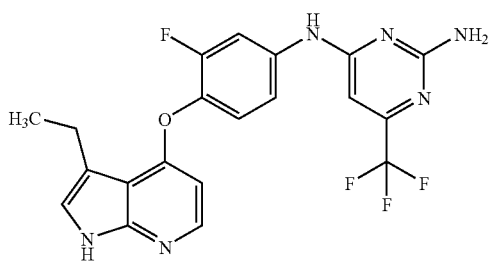

45 mg (0.17 mmol) of 4-[(3-ethyl-1H-pyrrolo[2,3-b]pyridin-4-yl)oxy]-3-fluoroaniline and 34 mg (0.17 mmol) of 4-chloro-6-trifluoromethyl)pyrimidine-2-amine are suspended in 5 ml of water. 24 μl of 37% strength hydrochloric acid are added, and the mixture is heated at reflux overnight. Another 70 mg (0.35 mmol) of 4-chloro-6-(trifluoromethyl)pyrimidine-2-amine and 40 μl of 37% strength hydrochloric acid are then added, and the mixture is heated at reflux for another night. Using 1N aqueous sodium hydroxide solution, the pH is then adjusted to 10. The mixture is concentrated under reduced pressure and the residue is purified by column chromatography on silica gel (mobile phase: dichloromethane/methanol 100:1 to 10:1). The product obtained is purified further by preparative HPLC.

Yield: 9.6 mg (13% of theory)
LC-MS (Method 3): $R_t$=2.12 min.
MS (ESI pos.): m/z=433 (M#H)$^+$.
$^1$H-NMR (DMSO-d$_6$, 400 MHz): δ=1.28 (t, 3H), 2.83 (q, 2H), 6.17 (d, 1H), 6.38 (s, 1H), 7.00 (br. s, 2H), 7.15 (br. s, 1H), 7.28-7.40 (m, 2H), 7.99 (d, 1H), 8.23 (dd, 1H), 9.88 (s, 1H), 11.40 (br. s, 1H).

Example 14

2-(4-{4-[(2-Amino-6-chloropyrimidin-4-yl)amino]-2-fluorophenoxy}-1H-pyrrolo[2,3-b]pyridin-3-yl)ethanol

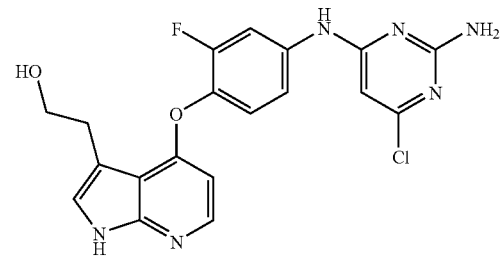

56 mg (0.17 mmol) of 2-[4-(4-amino-2-fluorophenoxy)-1H-pyrrolo[2,3-b]pyridin-3-yl]ethanol and 30 mg (0.18 mmol) of 4,6-dichloropyrimidine-2-amine are suspended in 5 ml of water. 25 μl of 37% strength hydrochloric acid are added, and the mixture is heated at reflux overnight. Using 1N aqueous sodium hydroxide solution, the pH is then adjusted to 10, resulting in the precipitation of crystals. The mixture is concentrated and filtered through silica gel. The product is purified by preparative HPLC.

Yield: 16 mg (22% of theory)
LC-MS (Method 3): Et=1.52 min.
MS (ESI pos.): m/z=415 (M+H)$^+$.
$^1$H-NMR (DMSO-d$_6$, 300 MHz): δ=2.97 (t, 2H), 3.70 (dt, 2H), 4.52 (t, 1H), 6.04 (s, 1H), 6.15 (d, 1H), 6.84 (br. s, 2H), 7.17 (d, 1H), 7.25-7.37 (m, 2H), 7.98 (d, 1H), 8.15 (dd, 1H), 9.58 (s, 1H), 11.41 (br. s, 1H).

Example 15

2-[4-(4-{[2-Amino-6-(trifluoromethyl)pyrimidin-4-yl]amino}-2-fluorophenoxy)-1H-pyrrolo[2,3-b]pyridin-3-yl]ethanol

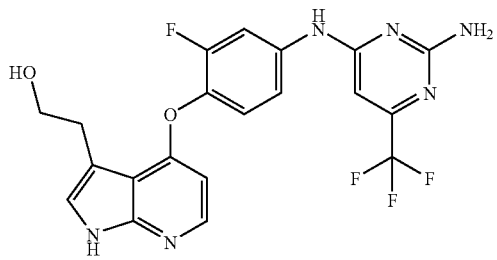

130 mg (0.45 mmol) of 2-[4-(4-amino-2-fluorophenoxy)-1H-pyrrolo[2,3-b]pyridin-3-yl]ethanol and 107 mg (0.54 mmol) of 4-chloro-6-(trifluoromethyl)pyrimidine-2-amine are suspended in 6 ml of water. 0.6 ml (0.6 mmol) of 1N hydrochloric acid is added and the mixture is heated at reflux overnight. Using 1N aqueous sodium hydroxide solution, the suspension is adjusted to pH 10, resulting in the precipitation of crystals. The crystals are filtered off with suction, washed with water and purified by column chromatography on silica gel (mobile phase: dichloromethane/methanol (7N ammonia) 100:1 to 100:3).

Yield: 170 mg (80% of theory)
LC-MS (Method 1): $R_t$=1.54 min.
MS (ESI pos.): m/z=449 (M+H)$^+$.
$^1$H-NMR (DMSO-$d_6$, 400 MHz): δ=2.97 (t, 2H), 3.70 (dt, 2H), 4.58 (t, 1H), 6.16 (d, 1H), 6.38 (s, 1H), 7.10 (br. s, 2H), 7.18 (d, 1H), 7.29-7.41 (m, 2H), 7.98 (d, 1H), 8.24 (dd, 1H), 9.89 (s, 1H), 11.46 (br. s, 1H).

Example 16

2-(4-{4-[(2-Aminopyrimidin-4-yl)amino]-2-fluorophenoxy}-1H-pyrrolo[2,3-b]pyridin-3-yl)ethanol

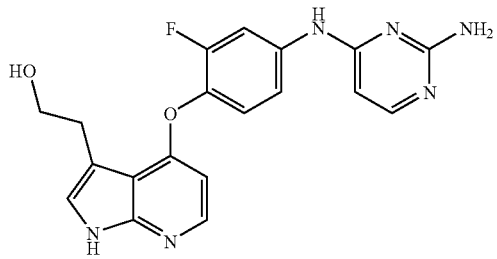

135 mg (0.47 mmol) of 2-[4-(4-amino-2-fluorophenoxy)-1H-pyrrolo[2,3-b]pyridin-3-yl]ethanol and 79 mg (0.61 mmol) of 4-chloropyrimidine-2-amine are suspended in 6 ml of water. 0.6 ml (0.6 mmol) of 1N hydrochloric acid is added, and the mixture is heated at reflux overnight. Using 1N aqueous sodium hydroxide solution, the suspension is adjusted to pH 10, resulting in the precipitation of crystals. The crystals are filtered off with suction, washed with water and purified by column chromatography on silica gel (mobile phase: dichloromethane/methanol (7N ammonia) 100:1 to 10:1).

Yield: 158 mg (88% of theory)
LC-MS (Method 1): $R_t$=0.88 min.
MS (ESI neg.): m/z=379 (M−H)$^−$.
$^1$H-NMR (DMSO-$d_6$, 400 MHz): δ=2.97 (t, 2H), 3.70 (dt, 2H), 4.58 (t, 1H), 6.02 (d, 1H), 6.14 (d, 1H), 6.36 (br. s, 2H), 7.17 (d, 1H), 7.24-7.40 (m, 2H), 7.86 (d, 1H), 7.98 (d, 1H), 8.22 (dd, 1H), 9.41 (s, 1H), 11.44 (br. s, 1H).

Example 17

$N^4$-(3-Fluoro-4-{[3-(2-methoxyethyl)-1H-pyrrolo[2,3-b]pyridin-4-yl]oxy}phenyl)-6-(trifluoromethyl)pyrimidine-2,4-diamine

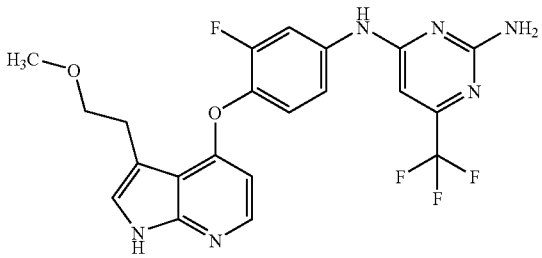

53 mg (0.18 mmol) of 3-fluoro-4-{[3-(2-methoxyethyl)-1H-pyrrolo[2,3-b]pyridin-4-yl]oxy}aniline and 42 mg (0.21 mmol) of 4-chloro-6-(trifluoromethyl)pyrimidine-2-amine are suspended in 4 ml of water. 0.23 ml (0.23 mmol) of 1N hydrochloric acid is added, and the mixture is heated at reflux overnight. Another 22 mg (0.11 mmol) of 4-chloro-6-trifluoromethyl)pyridine-2-amine are then added, and the mixture is again heated overnight. By addition of 1N aqueous sodium hydroxide solution, the pH is adjusted to 10, resulting in the precipitation of crystals. The crystals are filtered off with suction and washed with water. The product is purified by preparative HPLC.

Yield: 45 mg (55% of theory)
LC-MS (Method 1): $R_t$=1.88 min.
MS (ESI pos.): m/z=463 (M+H)$^+$.
$^1$H-NMR (DMSO-$d_6$, 300 MHz): δ=3.04 (t, 2H), 3.25 (s, 3H), 3.64 (t, 2H), 6.19 (d, 1H), 6.38 (s, 1H), 6.96 (br. s, 2H), 7.20 (d, 1H), 7.28-7.42 (m, 2H), 8.00 (d, 1H), 8.22 (dd, 1H), 9.85 (s, 1H), 11.46 (br. s, 1H).

Example 18

4-(4-{[2-Amino-6-(trifluoromethyl)pyrimidin-4-yl]amino}-2-fluorophenoxy)-1H-pyrrolo[2,3-b]pyridin-3-carbonitrile

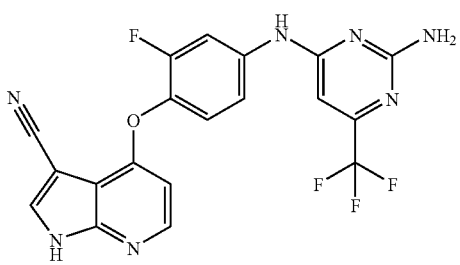

19.0 mg (0.071 mmol) of 4-(4-amino-2-fluorophenoxy)-1H-pyrrolo[2,3-b]pyridine-3-carbonitrile and 19.6 mg (0.099 mmol) of 4-chloro-6-(trifluoromethyl)pyrimidine-2-amine are suspended in 5 ml of water. 0.1 ml (0.1 mmol) of 1N hydrochloric acid is added, and the mixture is heated at reflux overnight. 3 ml of ethanol and a further 19.6 mg (0.099 mmol) of 4-chloro-6-(trifluoromethyl)pyrimidine-2-amine are then added. The mixture is stirred at 100° C. for another 6 hours. The mixture is concentrated slightly and the pH is adjusted to 10 using 1N aqueous sodium hydroxide solution, resulting in the precipitation of crystals. The crystals are filtered off with suction, washed with water and purified by column chromatography on silica gel (mobile phase: dichloromethane/methanol (7N ammonia) 100:1 to 10:1).

Yield: 24 mg (77% of theory)
LC-MS (Method 1): $R_t$=1.93 min.
MS (ESI pos.): i/z=430 (M+H)$^+$.
$^1$H-NMR (DMSO-d$_6$, 300 MHz): δ=6.39 (s, 1H), 6.44 (d, 1H), 7.04 (br. s, 2H), 7.40-7.43 (m, 2H), 8.22 (d, 1H), 8.29 (d, 1H), 8.43 (s, 1H), 9.93 (s, 1H), 12.93 (br. s, 1H).

Example 19

4-(4-{[2-Amino-6-chloropyrimidin-4-yl]amino}-2-fluorophenoxy)-1H-pyrrolo[2,3-b]pyridine-3-carbonitrile

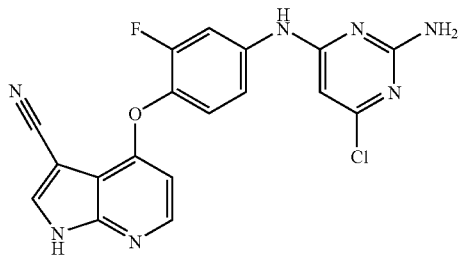

49.0 mg (0.18 mmol) of 4-(4-amino-2-fluorophenoxy)-1H-pyrrolo[2,3-b]pyridine-3-carbonitrile and 33.0 mg (0.20 mmol) of 4,6-dichloropyrimidine-2-amine are suspended in 5 ml of water. 0.12 ml (0.24 mmol) of 2N hydrochloric acid is added, and the mixture is heated at reflux overnight. Using concentrated aqueous sodium hydroxide solution, the mixture is made alkaline, and the product is purified by preparative HPLC.

Yield: 40 mg (54% of theory)
LC-MS (Method 3): $R_t$=2.05 min.
MS (ESI pos.): m/z=396 (M+H)$^+$.
$^1$H-NMR (DMSO-d$_6$, 400 MHz): o=6.05 (s, 1H), 6.41 (d, 1H), 6.89 (br. s, 2H), 7.37 (m, 2H), 8.18-8.24 (m, 2H), 8.38 (s, 1H), 9.68 (s, 1H), 13.00 (br. s, 1H).

Example 20

4-{4-[(2-Aminopyrimidin-4-yl)amino]-2-fluorophenoxy}-1H-pyrrolo[2,3-b]pyridine-3-carbonitrile

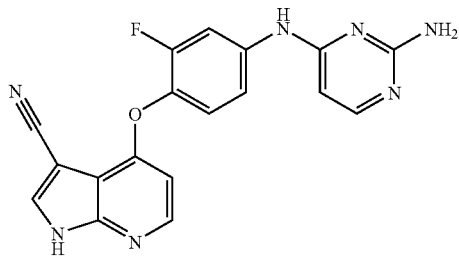

200 mg (0.66 mmol) of 4-(4-amino-2-fluorophenoxy)-1H-pyrrolo[2,3-b]pyridine-3-carbonitrile and 104 mg (0.72 mmol) of 4-chloropyrimidine-2-amine are suspended in 9 ml of water and 4.5 ml of ethanol. 0.33 ml (1.31 mmol) of 4N hydrochloric acid is added, and the mixture is heated at reflux for 2 h. The mixture is made alkaline using concentrated aqueous sodium hydroxide solution, diluted with water and extracted with ethyl acetate. The organic phase is separated off and concentrated. The crude product is purified by preparative HPLC. This gives the title compound as crystals.

Yield: 81 mg (34% of theory)
LC-MS (Method 1): $R_t$=1.24 min.
MS (ESI pos.): m/z=362 (M+H)+
$^1$H-NMR (DMSO-d$_6$, 400 MHz): δ=−6.03 (d, 1H), 6.36 (br. s, 2H), 6.42 (d, 1H), 7.32-7.43 (m, 2H), 7.86 (d, 1H), 8.21 (d, 1H), 8.26 (dd, 1H), 8.41 (s, 1H), 9.44 (s, 1H), 12.90 (s, 1H).

Example 21

4-{4-[(2-Aminopyrimidin-4-yl)amino]-2,6-difluorophenoxy}-1H-pyrrolo[2,3-b]pyridine-3-carbonitrile

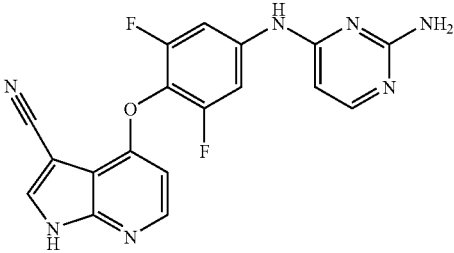

250 mg (0.65 mmol) of 4-(4-amino-2,6-difluorophenoxy)-1H-pyrrolo[2,3-b]pyridine-3-carbonitrile and 92 mg (0.71 mmol) of 4-chloropyrimidine-2-amine are suspended in 10 ml of water and 5 ml of ethanol. 0.32 ml (1.29 mmol) of 4N hydrochloric acid is added, and the mixture is heated at reflux for 2 h. The mixture is made alkaline using concentrated aqueous sodium hydroxide solution, diluted with water and extracted with ethyl acetate. The organic phase is separated off and concentrated. The crude product is purified by preparative HPLC. This gives the title compound as crystals.

Yield: 138 mg (56% of theory)
LC-MS (Method 2): $R_t$=1.48 min.
MS (ESI pos.): m/z=380 (M+H)$^+$.
$^1$H-NMR (DMSO-d$_6$, 400 MHz): δ=6.03 (d, 1H), 6.49 (br. s, 2H), 6.54 (d, 1H), 7.82 (d, 2H), 7.91 (d, 1H), 8.24 (d, 1H), 8.45 (s, 1H), 9.61 (s, 1H), 12.98 (br. s, 1H).

Example 22

N$^4$-{4-[(3-Cyclopropyl-1H-pyrrolo[2,3-b]pyridin-4-yl)oxy]-3,5-difluorophenyl}-6-(trifluoromethyl)-pyrimidine-2,4-diamine

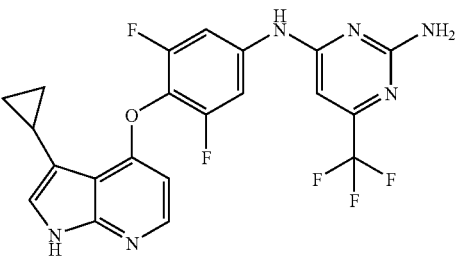

330 mg (1.10 mmol) of 4-[(3-cyclopropyl-1H-pyrrolo[2,3-b]pyridin-4-yl)oxy]-3,5-difluoroaniline and 320 mg (1.64 mmol) of 4-chloro-6-(trifluoromethyl)pyrimidine-2-amine are suspended in 4 ml of water and 2 ml of ethanol. 0.55 ml (2.2 mmol) of 4N hydrochloric acid is added, and the mixture is heated at reflux for 1 h. Another 107 mg (0.55 mmol) of 4-chloro-6-(trifluoromethyl)pyrimidine-2-amine are then added, and the mixture is heated for a further 2 hours. The mixture is made alkaline by addition of 1N aqueous sodium hydroxide solution and extracted with ethyl acetate, and the organic phase is washed with water. The organic phase is dried over sodium sulfate and the solvent is removed under reduced pressure. The product is purified by preparative HPLC.

Yield: 340 mg (65% of theory)

LC-MS (Method 2): R=2.45 min.

MS (ESI pos.): m/z=463 (M+H)$^+$.

$^1$H-NMR (DMSO-d$_6$, 300 MHz): δ=0.61-0.68 (m, 2H), 0.81-0.89 (m, 2H), 2.14-2.25 (m, 1H), 6.25 (d, 1H), 6.38 (s, 1H), 7.09 (d, 1H), 7.12 (br. s, 2H), 7.79 (d, 2H), 8.01 (d, 1H), 10.05 (br. s, 1H), 11.48 (br. s, 1H).

Example 23

6-Chloro-N$^4$-{4-[(3-chloro-1H-pyrrolo[2,3-b]pyridin-4-yl)oxy]-3,5-difluorophenyl}pyrimidine-2,4-diamine

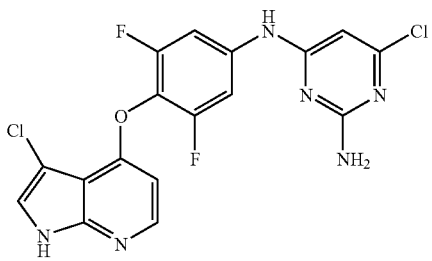

162 mg (0.55 mmol) of 3,5-difluoro-4-[(3-chloro-1H-pyrrolo[2,3-b]pyridin-4-yl)oxy]aniline and 90 mg (0.55 mmol) of 4,6-dichloropyrimidine-2-amine are suspended in 6 ml of water/ethanol 1:1. 56 μl (0.65 mmol) of 37% strength hydrochloric acid are added, and the mixture is heated at reflux for 3 h. Using 1N aqueous sodium hydroxide solution, the pH is adjusted to 7, and the mixture is extracted with ethyl acetate. The organic phase is washed with saturated sodium chloride solution, dried over magnesium sulfate and concentrated. The residue is purified by preparative HPLC.

Yield: 79 mg (34% of theory)

HPLC (Method 3): R$_t$=2.38 min.

MS (ESI pos.): m/z=405, 407 (M+H)$^+$.

$^1$H-NMR (DMSO-d$_6$, 300 MHz): δ=6.04 (s, 1H), 6.35 (d, 1H), 7.00 (br. s, 2H), 7.61 (s, 1H), 7.75 (d, 2H), 8.10 (d, 1H), 9.80 (s, 1H), 12.13 (br. s, 1H).

Example 24

N$^4$-{4-[(3-Chloro-1H-pyrrolo[2,3-b]pyridin-4-yl)oxy]-3,5-difluorophenyl}pyrimidine-2,4-diamine

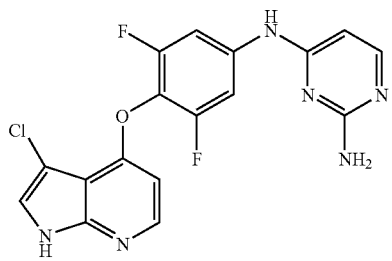

200 mg (0.67 mmol) of 3,5-difluoro-4-[(3-chloro-1H-pyrrolo[2,3-b]pyridin-4-yl)oxy]aniline and 88 mg (0.67 mmol) of 4-chloropyrimidine-2-amine are suspended in 6 ml of water/ethanol 1:1. 69 μl (0.81 mmol) of 37% strength hydrochloric acid are added, and the mixture is heated at reflux for 3 h. Using 1N aqueous sodium hydroxide solution, the pH is adjusted to 7, and the mixture is extracted with ethyl acetate. The organic phase is washed with saturated sodium chloride solution, dried over magnesium sulfate and concentrated. The residue is purified by preparative HPLC.

Yield: 93 mg (35% of theory)

HPLC (Method 2): R=1.63 min.

MS (ESI pos.): m/z=405, 407 (M+H)$^+$.

$^1$H-NMR (DMSO-d$_6$, 300 MHz): δ=6.02 (d, 1H), 6.35 (d, 1H), 6.47 (br. s, 2H), 7.61 (s, 1H), 7.79 (d, 2H), 7.90 (d, 1H), 8.10 (d, 1H), 9.58 (s, 1H), 12.12 (br. s, 1H).

Example 25

N-{4-[(3-Bromo-1H-pyrrolo[2,3-b]pyridin-4-yl)oxy]-3,5-difluorophenyl}-6-(trifluoromethyl)pyrimidine-2,4-diamine

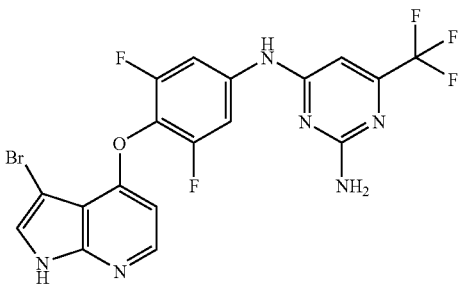

47 mg (0.14 mmol) of 4-[(3-bromo-1H-pyrrolo[2,3-b]pyridin-4-yl)oxy]-3,5-difluoroaniline and mg (0.18 mmol) of 4-chloro-6-trifluoromethyl)pyrimidine-2-amine are suspended in a mixture of 5 ml of water and 1 ml of ethanol. 0.18 ml of 1M hydrochloric acid is added, and the mixture is heated at 100° C. overnight. Using 1N aqueous sodium hydroxide solution, the suspension is then adjusted to pH 10, resulting the precipitation of crystals. The solid is filtered off and washed with water. The crude product is purified by preparative HPLC.

Yield: 18 mg (26% of theory)
LC-MS (Method 2): $R_t$=2.50 min.
MS (ESI neg.): m/z=499 (M−H)⁻.
$^1$H-NMR (CD$_3$OD/CD$_2$Cl$_2$ 1:1, 400 MHz): δ=5.48 (s, 2H), 6.36 (d, 1H), 6.42 (s, 1H), 7.37 (s, 1H), 7.68 (d, 2H), 8.06 (d, 1H).

B. Assessment of the Physiological Activity

The inhibition of the enzyme is investigated in an in vitro assay with recombinant Rho kinase II. The vessel-relaxing action is determined using phenylephrine-induced contractions of isolated rings of the saphenous artery of rabbits. The suitability of the compounds according to the invention for treating cardiovascular disorders can be demonstrated by examining the hypotensive effect on anesthetized rats.

Inhibition of Recombinant Rho Kinase II (ROKα)

The activity of Rho kinase is determined by the uptake of $^{33}$P phosphate into a substrate peptide. To this end, commercially available Rho kinase 1 (Upstate Biotechnology) is preincubated at 37° C. in the presence of the S6 phosphate-acceptor peptide with the test substances or a solvent control for 10 min. The kinase reaction is then started by addition of $^{33}$P-labeled ATP. After 20 min at 37° C., the reaction is stopped by addition of H$_3$PO$_4$. Aliquots are pipetted onto filters and the filters are washed and then covered with scintillator. The radioactivity of the $^{33}$P-labeled peptides bound to the filter is measured in a Micro-Beta counter. The IC$_{50}$ value corresponds to the concentration of a test substance at which the Rho-kinase-catalyzed uptake of $^{33}$P into the peptide is inhibited by 50%, compared to a solvent control. The experimental data are summarized in Table A below.

TABLE A

| Example No. | IC$_{50}$ (nM) |
|---|---|
| 1 | 2 |
| 5 | 7 |
| 9 | 4 |
| 18 | 2 |

Vessel-Relaxing Action In Vitro

Individual 3-mm-wide rings of the isolated saphenous artery of rabbits are introduced into 5 ml organ baths with Krebs-Henseleit solution (37° C., gassed with carbogen). The vessel tone is monitored isometrically and registered. Contractions are induced by addition of 3×1.04 g of phenylephrine/ml, which is washed out again after 4 min. After a number of control cycles, the rings are preincubated with the substance to be examined, with the dosage being increased for each further cycle, and the subsequent contraction is compared to the intensity of the last control contraction. The concentration required to reduce the intensity of the control value by 50% (IC$_{50}$) is calculated. The experimental data are summarized in Table B below.

TABLE B

| Example No. | IC$_{50}$ (nM) |
|---|---|
| 1 | 67 |
| 5 | 100 |
| 9 | 45 |
| 18 | 19 |

Measurement of Blood Pressure in Anesthetized Rats

Male Wistar rats of a body weight of 300-350 g are anesthetized with thiopental (100 mg/kg i.p.). Following tracheotomy, a catheter is introduced into the femoral artery to measure the blood pressure. The substances to be tested are administered as solutions, either orally via a stomach tube or intravenously via the femoral vein.

Inhibition of Cytochrome P-450 Enzymes (CYP Assay)

The potential of inhibiting the metabolically important P-450 isoenzymes (1A2, 2C9, 2D6 and 3A4) is examined in an automized manner in the 96-well format. The enzyme source used are human liver microsomes, and the CYP isoform-selective substrates are phenacetin (CYP1A2), diclofenac (CYP2C9), dextromethorphan (CYP2D6) and midazolam (CYP3A4). The formation of the metabolites in question from the respective standard substrates is measured by LC-MS/MS as a function of the inhibitor concentration, and the IC$_{50}$ values are calculated. The effect on metabolite formation at a defined substrate concentration and 6 concentrations of the potential inhibitors is examined. As positive control, a known inhibitor of the respective CYP isoform examined is also tested on each microtiter plate. Additionally, in the case of the CYP3A4 assay, the inhibition following preincubation of the potential inhibitors with human liver microsomes in the presence of NADPH is tested.

Experimental details are summarized in Table C:

TABLE C

| CYP | Substrate (concentration) | Protein [mg/ml] | Incubation time [min] | ISTD | Standard inhibitor |
|---|---|---|---|---|---|
| 1A2 | phenacetin (30 μM) | 0.3 | 20 | D$_3$-acetaminophen | fluvoxamine |
| 2C9 | diclofenac (10 μM) | 0.05 | 15 | tolbutamide | sulfaphenazole |
| 2D6 | dextromethorphan (10 μM) | 0.5 | 20 | quinidine | fluoxetine |
| 3A4 | midazolam (10 μM) | 0.2 | 15 | oxazepam | ketoconazole |
|  | with preincubation | 0.2 | 15/15 | oxazepam | troleandomycin |

The incubations are carried out in phosphate buffer (100 mM, pH 7.4) on microtiter plates (96 wells, volume 200 μl). Incubation time and protein content of the incubations depend on the substrate used and are summarized in Table C. Following addition of 100 μl of acetonitrile (comprising the respective internal standard), the precipitated proteins are removed by centrifugation on a filter plate. The supernatants are combined and the samples are analyzed by LC-MS/MS.

C. Working Examples for Pharmaceutical Compositions

The compounds according to the invention can be converted into pharmaceutical preparations as follows:

Tablet:
Composition:
100 mg of the compound from Example 1, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg. Diameter 8 mm, spherical radius 12 mm.

Preparation:
The mixture of inventive compound, lactose and starch is granulated with a 5% strength solution (w/w) of the PVP in water. After drying, the granules are mixed for 5 min with the magnesium stearate. This mixture is compacted in a conventional tablet press (dimensions of the tablet: see above). The standard value used for compacting is a compaction force of 15 kN.

Suspension for Oral Administration:
Composition:
1000 mg of the compound from Example 1, 1000 mg of ethanol (96%), 400 mg of Rhodigel (xanthan gum from FMC, Pennsylvania, USA) and 99 g of water.

A single dose of 100 mg of the compound according to the invention corresponds to 10 ml of oral suspension.

Preparation:
The Rhodigel is suspended in ethanol and the active compound is added to the suspension. The water is added with stirring. The mixture is stirred for about 6 h until the Rhodigel is completely swollen.

The invention claimed is:

1. A compound of the formula (I)

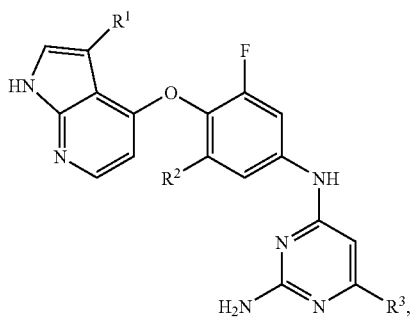

in which
$R^1$ represents chlorine, cyano, methyl, ethyl, hydroxyethyl, methoxyethyl or cyclopropyl,
$R^2$ represents hydrogen or fluorine, and
$R^3$ represents hydrogen, chlorine, trifluoromethyl or pentafluoroethyl, or a salt thereof.

2. The compound as claimed in claim 1,
in which
$R^1$ represents chlorine, cyano, methyl, ethyl, hydroxyethyl, methoxyethyl or cyclopropyl,
$R^2$ represents hydrogen or fluorine, and
$R^3$ represents hydrogen, chlorine or trifluoromethyl, or a salt thereof.

3. The compound as claimed in claim 1,
in which
$R^1$ represents cyano, methyl or hydroxyethyl,
$R^2$ represents hydrogen or fluorine, and
$R^3$ represents chlorine or trifluoromethyl,
or a salt thereof.

4. A process for preparing a compound of the formula (I) as defined in claim 1, characterized in that
a compound of the formula (II)

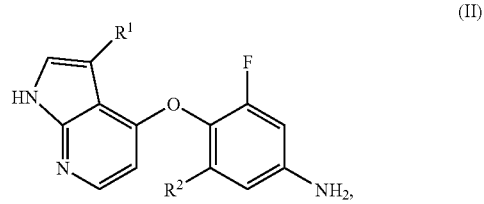

in which
$R^1$ and $R^2$ are as defined in claim 1 is reacted with a compound of the formula (III)

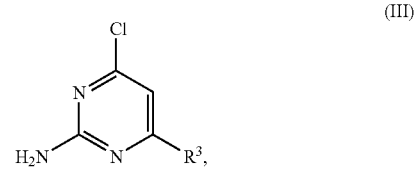

in which
$R^3$ is as defined in claim 1.

5. A method for the treatment of erectile dysfunction comprising administering an effective amount of a compound of the formula (I) as defined in claim 1.

6. A method for the treatment of hypertension, comprising administering an effective amount of a compound of the formula (I) as defined in claim 1.

7. A pharmaceutical composition, comprising a compound of the formula (I) as defined in claim 1 in combination with a further active compound.

8. A pharmaceutical composition comprising a compound of the formula (I) as defined in claim 1 in combination with an inert nontoxic pharmaceutically acceptable auxiliary.

* * * * *